(12) United States Patent
Kourtz et al.

(10) Patent No.: US 7,732,680 B2
(45) Date of Patent: Jun. 8, 2010

(54) CHEMICALLY INDUCIBLE EXPRESSION OF BIOSYNTHETIC PATHWAYS

(75) Inventors: Lauralynn Kourtz, Arlington, MA (US); Oliver P. Peoples, Arlington, MA (US); Kristi D. Snell, Belmont, MA (US)

(73) Assignee: Metabolix, Inc., Cambridge, MA (US)

( * ) Notice: Subject to any disclaimer, the term of this patent is extended or adjusted under 35 U.S.C. 154(b) by 412 days.

(21) Appl. No.: 11/376,831

(22) Filed: Mar. 16, 2006

(65) Prior Publication Data

US 2007/0067869 A1 Mar. 22, 2007

Related U.S. Application Data

(60) Provisional application No. 60/662,235, filed on Mar. 16, 2005, provisional application No. 60/669,766, filed on Apr. 8, 2005.

(51) Int. Cl.
*A01H 5/00* (2006.01)
*C12N 15/08* (2006.01)
*C12N 15/31* (2006.01)
*C12N 15/82* (2006.01)

(52) U.S. Cl. ........................ 800/320; 800/288; 800/298; 800/306; 800/312; 800/314; 800/320.1; 800/317.3; 800/322; 435/320.1; 435/419

(58) Field of Classification Search ........................ None
See application file for complete search history.

(56) References Cited

U.S. PATENT DOCUMENTS

| | | | |
|---|---|---|---|
| 4,876,331 A | 10/1989 | Doi | 528/361 |
| 5,000,000 A | 3/1991 | Ingram et al. | 435/161 |
| 5,004,863 A | 4/1991 | Umbeck | 800/314 |
| 5,015,580 A | 5/1991 | Christou et al. | 800/267 |
| 5,015,944 A | 5/1991 | Bubash | 324/127 |
| 5,024,944 A | 6/1991 | Collins et al. | 800/294 |
| 5,030,572 A | 7/1991 | Power et al. | 435/428 |
| 5,034,322 A | 7/1991 | Rogers et al. | 435/252.2 |
| 5,102,797 A | 4/1992 | Tucker et al. | 435/172.3 |
| 5,159,135 A | 10/1992 | Umbeck | 800/314 |
| 5,169,770 A | 12/1992 | Chee et al. | 800/294 |
| 5,231,019 A | 7/1993 | Paszkowski et al. | 435/470 |
| 5,268,463 A | 12/1993 | Jefferson | 536/23.7 |
| 5,276,268 A | 1/1994 | Strauch et al. | 800/288 |
| 5,292,860 A | 3/1994 | Shiotani et al. | 528/361 |
| 5,322,783 A | 6/1994 | Tomes et al. | 800/293 |
| 5,371,002 A | 12/1994 | Dennis et al. | 435/142 |
| 5,384,253 A | 1/1995 | Krzyzek et al. | 800/292 |
| 5,416,011 A | 5/1995 | Hinchee et al. | 800/294 |
| 5,464,765 A | 11/1995 | Coffee et al. | 435/470 |
| 5,470,727 A | 11/1995 | Mascarenhas et al. | 435/172.3 |
| 5,472,869 A | 12/1995 | Krzyzek et al. | 435/412 |
| 5,512,456 A | 4/1996 | Dennis | 435/69.1 |
| 5,519,164 A | 5/1996 | Mullner et al. | 800/285 |
| 5,527,695 A | 6/1996 | Hodges et al. | 800/291 |
| 5,530,196 A | 6/1996 | Fraley et al. | 800/298 |
| 5,534,432 A | 7/1996 | Peoples et al. | 435/240.4 |
| 5,538,877 A | 7/1996 | Lundquist et al. | 800/265 |
| 5,538,880 A | 7/1996 | Lundquist et al. | 800/265 |
| 5,545,818 A | 8/1996 | McBride et al. | 800/279 |
| 5,595,889 A | 1/1997 | Richaud et al. | 435/71.2 |
| 5,629,183 A | 5/1997 | Saunders et al. | 800/267 |
| 5,668,298 A | 9/1997 | Waldron | 800/288 |
| 5,750,848 A | 5/1998 | Kruger et al. | 800/281 |
| 5,767,378 A | 6/1998 | Bojsen et al. | 800/317.2 |

(Continued)

FOREIGN PATENT DOCUMENTS

EP     0 486 233     5/1992

(Continued)

OTHER PUBLICATIONS

Paddim, M., Current Opinion in Plant Biology 2003, vol. 6, pp. 169-177.*

(Continued)

*Primary Examiner*—Russell Kallis
(74) *Attorney, Agent, or Firm*—Pabst Patent Group LLP

(57) ABSTRACT

Methods and constructs for the introduction of multiple genes encoding enzymes in a multi-enzyme biosynthetic pathway are provided. In one embodiment, the constructs contain two or more enzyme-encoding genes, each under the control of an inducible promoter and each with a polyadenylation signal. The constructs are used to produce transgenic plants, in which the expression of the enzymes are increased when a chemical inducing agent is applied, and a biosynthetic product of the series of enzymes encoded by the transgenes is produced. Constructs may be used which contain two or more enzyme-encoding genes under the control of one or more promoters activated by activator molecules or complexes expressed from a transgene or transgenes, which are themselves under the control of one or more inducible promoters and switched on following the external application of a chemical. The transgene or transgenes expressing the activator molecules or complexes may be included in the same construct containing multiple genes encoding enzymes in a multi-enzyme biosynthetic pathway. Alternatively, the transgene or transgenes expressing the activator molecules or complexes may be on a different construct from the construct containing multiple genes encoding enzymes in a multi-enzyme biosynthetic pathway. The activator molecule can be expressed using a constitutive promoter in an inactive form which is converted to the active form following application of the chemical inducing agent.

26 Claims, 8 Drawing Sheets

U.S. PATENT DOCUMENTS

| | | | | |
|---|---|---|---|---|
| 5,849,894 | A | 12/1998 | Clemente et al. | 536/23.2 |
| 5,955,650 | A | 9/1999 | Hitz | 800/281 |
| 5,965,417 | A | 10/1999 | Chenivesse et al. | |
| 6,011,144 | A | 1/2000 | Steinbuchel et al. | 536/23.2 |
| 6,051,754 | A | 4/2000 | Knutzon | 800/281 |
| 6,140,486 | A | 10/2000 | Facciotti et al. | 536/23.2 |
| 6,316,262 | B1 | 11/2001 | Huisman et al. | 435/490 |
| 6,433,250 | B1 | 8/2002 | Somerville et al. | 800/281 |
| 6,448,473 | B1* | 9/2002 | Mitsky et al. | 800/278 |
| 6,586,658 | B1 | 7/2003 | Peoples et al. | 800/281 |
| 6,593,116 | B1 | 7/2003 | Huisman et al. | 435/135 |
| 6,635,451 | B2 | 10/2003 | Mukerji et al. | 435/71.1 |
| 6,835,820 | B2 | 12/2004 | Cannon et al. | 536/23.2 |
| 2004/0049805 | A1* | 3/2004 | Lerchl et al. | 800/281 |

FOREIGN PATENT DOCUMENTS

| | | |
|---|---|---|
| EP | 0 530 129 | 3/1993 |
| EP | 0 604 662 | 7/1994 |
| WO | WO 91/00917 | 1/1991 |
| WO | WO 94/00977 | 1/1994 |
| WO | WO 94/21810 | 9/1994 |
| WO | WO 98/00557 | 1/1998 |
| WO | WO 98/04713 | 2/1998 |
| WO | WO 98/06854 | 2/1998 |
| WO | WO 99/14313 | 3/1999 |
| WO | WO 00/06747 | 2/2000 |
| WO | WO 00/08198 | 2/2000 |
| WO | WO 00/10612 | 3/2000 |
| WO | WO 01/29204 | 4/2001 |
| WO | WO 01/34825 | 5/2001 |
| WO | WO 01/59091 | 8/2001 |
| WO | WO 02/33107 | 4/2002 |
| WO | WO 02/37951 | 5/2002 |
| WO | WO 02/037951 | 5/2002 |
| WO | WO 2004/071467 | 8/2004 |

OTHER PUBLICATIONS

Bohmert K. et al., Plant (2000); vol. 211, pp. 841-845.*

Abbadi, et al., "Biosynthesis of very-long-chain polyunsaturated fatty acids in transgenic oilseeds: constraints on their accumulation", *Plant Cell*, 16(10):2734-48 (2004).

Arai, et al., "Production of polyhydroxybutyrate by polycistronic expression of bacterial genes in tobacco plastid", *Plant Cell Physiol.*, 45(9):1176-84 (2004).

Dyer, et al., "Metabolic engineering of *Saccharomyces cerevisiae* for production of novel lipid compounds", *Appl. Microbiol. Biotechnol.*, 59(2-3):224-30 (2002).

Fussenegger, et al., "Novel cytostatic process enhances the productivity of Chinese hamster ovary cells", *Biotechnology and Bioengineering*, 55(6):927-939 (1997).

Fussenegger, et al., "Regulated overexpression of the survival factor bcl-2 in CHO cells increases viable cell density in batch culture and decreases DNA release in extended fixed-bed cultivation", *Cytotechnology*, 32(1):45-61 (2000).

Hong, et al., "Expression of the *Arabidopsis* feedback-insensitive anthranilate synthase holoenzyme and tryptophan decarboxylase genes in *Catharanthus roseus* hairy roots", *J. Biotechnology*, 122(1)28-38 (2006).

Hughes, et al., "Metabolic engineering of the indole pathway in *Catharanthus roseus* hairy roots and increased accumulation of tryptamine and serpentine", *Metab. Eng.*, (4):268-76 (2004).

Jadhav, et al., "Production of 22:2Δ5,Δ13 and 20:1Δ5 in *Brassica carinata* and soybean breeding lines via introduction of *Limnanthes* genes", *Molecular Breeding*, 15(2):157-167 (2005).

Lardizabal, et al., "Purification of a jojoba embryo wax synthase, cloning of its cDNA, and production of high levels of wax in seeds of transgenic *Arabidopsis*", *Plant Physiol.*, 122(3):645-55 (2000).

Thelen, et al., "Metabolic engineering of fatty acid biosynthesis in plants". *Metab. Eng.*, 4(1):12-21 (2002).

Weber, et al., "Versatile macrolide-responsive mammalian expression vectors for multiregulated multigene metabolic engineering", *Biotechnol. Bioeng.*, 80(6):691-705 (2002).

Zuo, et al., "Chemical-inducible systems for regulated expression of plant genes", *Curr. Opin. Biotechnol*, 11(2):146-51 (2000).

Abe, et al., "Biosynthesis from gluconate of a random copolyester consisting of 3-hydroxybutyrate and medium-chain-length 3-hydroxyalkanoates by *Pseudomonas* sp. 61-3.", *Int. J. Biol. Macromol.* 16:115-119 (1994).

Adams, et al., "Relationship between internalization and mRNA decay in down-regulation of recombinant type 1 angiotensin II receptor (AT1) expression in smooth muscle cells", *Mol. Pharmacol.*, 55(6)1028-1036 (1999).

Amos and McInerney, "Composition of poly-hydroxyalkanoate from *Syntrophomonas wolfei* grown on unsaturated fatty acid substrates", *Arch. Microbiol.* 155:103-06 (1991).

Aoyama and Chua, "Glucocorticoid-mediated transcriptional induction system in transgenic plants", *Plant J.*, 11:605-612 (1997).

Banjoko and Trelease, "Development and application of an in vivo plant peroxisome import system", *Plant Physiol.*, 107:1201-1208 (1995).

Baucher, et al., "Lignin:genetic engineering and impact on pulping", *Crit. Rev. Biochem. Mol. Biol.*, 38:305-350 (2003).

Bevan, et al., "Structure and transcription of the nopaline synthase gene region of T-DNA", *Nucleic Acids Res.*, 11(2):369-85 (1983).

Bohmert, et al., "Transgenic *Arabidopsis* plants can accumulate polyhydroxybutyrate to up to 4% of their fresh weight", *Planta*, 211, 841-5 (2000).

Bohmert, et. al., "Constitutive expression of the beta-ketothiolase gene in transgenic plants. A major obstacle for obtaining polyhydroxybutyrate-producing plants", *Plant Physiol.*, 128(4):1282-90. (2002).

Bohner, et al., "Technical advance:transcriptional activator TGV mediates dexamethasone-inducible and tetracycline-inactivatable gene expression", *Plant J.*, 19:87-95 (1999).

Brandl, et al., "Ability of the phototrophic bacterium *Rhodospirillum rubrum* to produce various poly (beta-hydroxyalkanoates): potential sources for biodegradable polyesters", *Int. J. Biol. Macromol.* 11:49-55 (1989).

Braunegg, et al., "Polyhydroxyalkanoates, biopolyesters from renewable resources: physiological and engineering aspects", *J. Biotech.* 65:127-161 (1998).

Brown, et al., "Cloning and characterization of the katB gene of *Pseudomonas aeruginosa* encoding a hydrogen peroxide-inducible catalase:purification of KatB, cellular localization, and demonstration that it is essential for optimal resistance to hydrogen peroxide", *J. Bacteriol.*, 177:6536-6544 (1995).

Bruce, et al., Expression profiling of the maize flavonoid pathway genes controlled by estradiol-inducible transcription factors CRC and P', *Plant Cell*, 12:65-80 (2000).

Caddick, et al., "An ethanol inducible gene switch for plants used to manipulate carbon metabolism", *Nature Biotechnol.*, 16:177-180 (1998).

Cevallos, et al., "Genetic and physiological characterization of a *Rhizobium etli* mutant strain unable to synthesize poly-beta-hydroxybutyrate", *J Bacteriol.* 178(6):1646-54 (1996).

Chiu, et al., "Engineered GFP as a vital reporter in plants", *Curr. Biol.*, 6: 325-30 (1996).

Clough and Bent, "Floral dip:a simplified method for Agrobacterium-mediated transformation of *Arabidopsis thaliana*", *Plant J.*, 16:735-43 (1998).

Coruzzi, et al., "Nucleotide sequences of two pea cDNA clones encoding the small subunit of ribulose 1,5-bisphosphate carboxylase and the major chlorophyll a/b-binding thylakoid polypeptide", *J Biol Chem.*, 258(3):1399-1402 (1983).

Cubitt, et al., "Understanding, improving and using green fluorescent proteins", *Trends Biochem Sci.*, 20 :448-455 (1995).

Dale and Ow, "Gene transfer with subsequent removal of the selection gene from the host genome", *Proc. Natl. Acad. Sci. USA*, 88:10558-10562 (1991).

De Lorenzo, et al., "Mini-Tn5 transposon derivatives for insertion mutagenesis, promoter probing, and chromosomal insertion of cloned DNA in gram-negative eubacteria", *J. Bacteriol.*, 172(11):6568-6572 (1990).

De Smet, et al., "Characterization of intracellular inclusions formed by *Pseudomonas oleovorans* during growth in octane", *J. Bacteriol.*, 154: 870-878 (1983).

De Veylder, et al., "Herbicide safener-inducible gene expression in *Arabidopsis thaliana*", *Plant Cell Physiol.*, 38:568-577 (1997).

Dirusso, "Primary sequence of the *Escherichia coli* fadBA operon, encoding the fatty acid-oxidizing multienzyme complex, indicates a high degree of homology to eucaryotic enzymes", *J. Bacteriol.*, 172:6459-6468 (1990).

Dmochowska, et al., "Structure and transcriptional control of the *Saccharomyces cerevisiae* POX1 gene encoding acyl-coenzyme A oxidase", *Gene*, 88:247-52 (1990).

Drexler, et al., "Metabolic engineering of fatty acids for breeding of new oilseed crops:strategies, problems and first results", *J Plant Physiol.*,160:779-802 (2003).

Falco, et al., "Transgenic canola and soybean seeds with increased lysine", *Biotechnology*, 13:577-82 (1995).

Fidler and Dennis, "Polyhydroxyalkanoate production in recombinant *Escherichia coli*", *FEMS Microbiol. Rev.*, 103: 231-236 (1992).

Franks and Birch, "Gene Transfer Into Intact Sugarcane Cells Using Microprojectile Bombardment", *Aust. J. Plant Physiol.*, 18:471-480 (1991).

Frey, et al., "Novel pristinamycin-responsive expression systems for plant cells", *Biotechnol. & Bioengineering*, 74:154-163 (2001).

Fukui and Doi, "Cloning and analysis of the poly(3-hydroxybutyrate-co-3-hydroxyhexanoate) biosynthesis genes of *Aeromonas caviae*", *J. Bacteriol .*, 179:4821-30 (1997).

Gasser and Fraley, "Genetically engineering plants for crop improvement", *Science*, 244:1293-99 (1989).

Gatz and Lenk, "Promoters that respond to chemical inducers" *Trends Plant Sci.*, 3:352-8 (1998).

Gatz and Quail, "Tn10-encoded tet repressor can regulate an operator-containing plant romoter" , *Proc. Natl. Acad. Sci. USA*, 85:1394-1397 (1988).

Goff, et al., "Transactivation of anthocyanin biosynthetic genes following transfer of B regulatory genes into maize tissues", *EMBO J*, 9:2517-2522 (1990).

Gossen and Bujard, "Tight control of gene expression in mammalian cells by tetracycline-responsive promoters", *Proc Natl Acad Sci USA*, 89:5547-5551 (1992).

Gremillon, et al., "New plant growth-modifying properties of the *Agrobacterium* T-6b oncogene revealed by the use of a dexamethasone-inducible promoter", *Plant J.*, 37:218-228 (2004).

Guo, et al., "A chemical-regulated inducible RNAi system in plants", *Plant J.*, 34:383-392 (2003).

Hall, et al., "Cloning of the *Nocardia corallina* polyhydroxyalkanoate synthase gene and production of poly-(3-hydroxybutyrate-co-3-hydroxyhexanoate) and poly-(3-hydroxyvalerate-co-3-hydroxyheptanoate)", *Can. J. Microbiol.*, 44:687-91 (1998).

Hamilton, et al., "New method for generating deletions and gene replacements in *Escherichia coli*", *J. Bacteriol.*, 171(9):4617-4622 (1989).

Hein, et al., "Biosynthesis of poly(4-hydroxybutyric acid) by recombinant strains of *Escherichia coli*", *FEMS Microbiol. Lett.*, 153:411-418 (1997).

Herrero, et al., "Transposon vectors containing non-antibiotic resistance selection markers for cloning and stable chromosomal insertion of foreign genes in gram-negative bacteria", *J. Bacteriol.*, 172:6557-6567 (1990).

Hoffmann, et al., "The *Pseudomonas aeruginosa* phaG gene product is involved in the synthesis of polyhydroxyalkanoic acid consisting of medium-chain-length constituents from non-related carbon sources", *FEMS Microbiology Letters*, 184:253-259 (2000).

Holt, et al., "Characterization of the safener-induced glutathione S-transferase isoform II from maize", *Planta*, 196(2):295-302 (1995).

Houmiel, et al., "Poly(beta-hydroxybutyrate) production in oilseed leukoplasts of *Brassica napus*", *Planta*, 209:547 -50 (1999).

Huisman, et al., "Metabolism of poly(3-hydroxyalkanoates) (PHAs) by *Pseudomonas oleovorans*. Identification and sequences of genes and function of the encoded proteins in the synthesis and degradation of PHA", *J. Biol. Chem.*, 266(4):2191-2198 (1991).

Hustede and Steinbüchel, "Characterization of the polyhydroxyalkanoate synthase gene locus of *Rhodobacter sphaeroides*", *Biotechnol. Lett.*, 15:709-14 (1993).

Hustede et. al., "Cloning of poly(3-hydroxybutyric acid) s ynthase genes of *Rhodobacter sphaeroides* and *Rhodospirillum rubrum* and heterologous expression in *Alcaligenes eutrophus*", *FEMS Microbiol. Lett*, 93: 285-90 (1992).

Itzhaki, et al., "Construction by gene targeting in human cells of a"conditional' CDC2 mutant that rereplicates its D', *Nat. Genet.*, 15:258-265 (1997).

Jefferson, et al., "GUS fusions: beta-glucuronidase as a sensitive and versatile gene fusion marker in higher plants", *EMBO J.*, 6:3901-3907 (1987).

Kaneko, et al, "Sequence analysis of the genome of the unicellular cyanobacterium *Synechocysti s* sp. strain PCC6803. II. Sequence determination of the entire genome and assignment of potential protein-coding regions", *DNA Res.*, 3(3):109-36 (1996).

Kato, et al., "Production of a novel copolymer of 3-hydroxybutyric acids and medium-chain-length 3-hydroxyalkanoic acids by *Pseudomonas* sp. 61-3 from sugars" *Appl. Microbiol. Biotechnol.*, 45:363-370 (1996).

Khoudi, et al., "An alfalfa rubisco small subunit homologue shares cis-acting elements with the regulatory sequences of the RbcS-3A gene from pea", *Gene*, 197:343-351 (1997).

Kidwell, et al., "Regulated expression of *Alcaligenes eutrophus* pha biosynthesis genes in *Escherichia coli*", *Appl. Environ. Microbiol.*, 61(4):1391-1398 (1995).

Kim, et al., "Production of poly-β-hydroxybutyrate by by fed-batch culture of recombinant *Escherichia coli*", *Biotechnol. Lett.*, 14:811-816 (1992).

Knutzon, et al., "Lysophosphatidic acid acyltransferase from coconut endosperm mediates the insertion of laurate at the sn-2 position of triacylglycerols in lauric rapeseed oil and can increase total laurate levels", *Plant Physiol.*, 120, 739-746 (1999).

Koncz and Schell, "The promoter of TL-DNA gene 5 controls the tissue-specific expression of chimaeric genes carried by a novel type of *Agrobacterium* vector", *Mol. Genetics Genomics*, 204: 383-396 (1986).

Koo, et al., "Ecdysone agonist-inducible expression of a coat protein gene from tobacco mosaic virus confers viral resistance in transgenic *Arabidopsis*", *Plant J.*, 37:439-448 (2004).

Kourtz, et al., "A novel thiolase-reductase gene fusion promotes the production of polyhydroxybutyrate in *Arabidopsis*", *Plant Biotechnol.*, 3:435-447 (2005).

Lafont and Dinan, "Practical uses for ecdysteroids for mammals including human: and update", *J. Insect Science*, 3:7 (2003).

Lageveen, et al., "Formation of polyesters by *Pseudomonas oleovorans*: effect of substrates on formation and composition of poly-(R)-3-hydroxyalkanoates and poly-(R)-3-hydroxyalkanoates", *Appl. Environ. Microbiol.*, 54:2924-2932 (1988).

Langenbach, et al., "Functional expression of the PHA synthase gene phaC1 from *Pseudomonas aeruginosa* in *Escherichia coli* results in poly(3-hydroxyalkanoate) synthesis", *FEMS Microbiol. Lett.*, 150(2):303-309 (1997).

Lawford and Rousseau, "The relationship between growth enhancement and pet expression in *Escherichia coli*", *Appl. Biochem. Biotechnol.*, 57-58:277-292 (1996).

Lee and Chang, "Production of poly(hydroxyalkanoic acid)", *Adv. Biochem. Eng. Biotechnol.*, 52:27-58 (1995).

Lee and Lee, "Enhanced production of poly(3-hydroxybutyrate) by filamentation-suppressed recombinant *Escherichia coli* in a defined medium", *J. Environ. Polymer Degrad.*, 4:131-134 (1996).

Lee, "Bacterial polyhydroxyalkanoates", *Biotech. Bioeng.*, 49:1-14 (1996).

Lee, et al., "Biosynthesis of copolymers consisting of 3-hydroxybutyric acid and medium-chain-length 3-hydroxylkanoic acids from 1,3-butanediol or from 3-hydroxybutyrate by *Pseudomonas* sp. A33", *Appl. Microbiol. Biotechnol.*, 42:901-909 (1995).

Lee, et al., "Stimulatory effects of amino acids and oleic acid on poly(3-hydroxybutyric acid) synthesis by recombinant *Escherichia coli*", *J. Ferment. Bioeng.*, 79: 177-180 (1995).

Lee, et al., "Comparison of recombinant *Escherichia coli* strains for synthesis and accumulation of poly-(3-hydroxybutyric acid) and morphological changes", *Biotechnol. Bioeng.*, 44:1337-1347 (1994).

Lee, et al., "Construction of plasmids, estimation of plasmid stability, and use of stable plasmids for the production of poly(3-hydroxybutyric acid) by recombinant *Escherichia coli*", *J. Biotechnol.*, 32(2):203-211 (1994).

Lee, et al., "Production of poly((β-hydroxybutyric acid) by recombinant *Escherichia coli*", *Ann. NY Acad. Sci.*, 721:43-53 (1994).

Lee, "Suppression of filamentation in recombinant *Escherichia coli* by amplified FtsA activity", *Biotechnol. Lett.*, 16:1247-1252 (1994).

Lemoigne and Roukhelman, "Fermetation β-hydroxybutyrique caracterisation et evolution des produits de deshydration et de polymerisation de l'acide β-dehydroxybutyrique", *Annales des fermentations*, 5:527-36 (1925).

Liebergesell and Steinbuchel, "Cloning and molecular analysis of the poly(3-hydroxybutyric acid) biosynthetic genes of *Thiocystis violacea*", *Appl Microbiol Biotechnol.*, 38(4):493-501 (1993).

Liebergesell and Steinbuchel, "Cloning and nucleotide sequences of genes relevant for biosynthesis of poly(3-hydroxybutyric acid) in *Chromatium vinosum* strain D", *Eur. J. Biochem.*, 209:135-150 (1992).

Lin, et al., "Spatially discrete, light-driven protein expression", *Chemistry & Biology*, 9:1347-1353 (2002).

Lloyd, et al., "Epidermal cell fate determination in *Arabidopsis*: patterns defined by a steroid-inducible regulator", *Science*, 266 :436-439 (1994).

Lokita, "The carboxy-terminal end of glycolate oxidase directs a foreign protein into tobacco leaf peroxisomes", *The Plant J.*, 361-366 (1991).

Madi and Prusky, "Sequence of a cDNA clone encoding an avocado (*Persea americana*) [Δ9]-stearoyl-acyl carrier protein desaturase )accession No. AF116861) (PGR 99-167)" *Plant Physiol.*, 121:1057 (1999).

Madison and Huisman, "Metabolic engineering of poly(3-hydroxyalkanoates): from DNA to plastic," *Microbiology and Molecular Biology Reviews*, 63:21-53 (1999).

Martinez, et al., "Creation of ecdysone receptor chimeras in plants for controlled regulation of gene expression", *Mol. Gen. Genet.*, 261:546-552 (1999).

Martinez, et al., "Ecdysone agonist inducible transcription in transgenic tobacco plants", *Plant J.*, 19:97-106 (1999).

Medberry, et al., "Intra-chromosomal rearrangements generated by Cre-lox site-specific recombination", *Nucleic Acids Res.*, 23:485-490 (1995).

Metcalf, et al., "Conditionally replicative and conjugative plasmids carrying *lac* Z alpha for cloning, mutagenesis, and allele replacement in bacteria", *Plasmid*, 35(1):1-13 (1996).

Mett, et al., "Copper-controllable gene expression system for whole plants", *Proc. Natl. Acad. Sci. USA*, 90:4567-4571 (1993).

Mori, et al. "Inducible high-level mRNA amplification system by viral replicase in transgenic plants", *Plant J.*, 27:79-86 (2001).

Nawrath, et al., "Targeting of the polyhydroxybutyrate biosynthetic pathway to the plastids of *Arabidopsis thaliana* results in high levels of polymer accumulation", *Proc. Natl. Acad. Sci. USA*, 91:12760 (1994).

Nishimura, et al., "Purification and properties of B-ketothiolase from *Zoogloea ramigera*", *Arch. Microbiol.*, 116(1):21-27 (1978).

Ouwerkerk, et al., "Glucocorticoid-inducible gene expression in rice" *Planta*, 213:370-378 (2001).

Padidam, Chemically regulated gene expression in plants', *Curr. Opin. Plant Biol.*, 6:169-177 (2003).

Pang, et al., "An improved green fluorescent protein gene as a vital marker in plants", *Plant Physiol.*, 112:893-900 (1996).

Panke, et al., "Engineering of quasi-natural *Pseudomonas putida* strains for toluene metabolism through an *ortho*-cleavage degradation pathway", *Appl. Environ. Microbiol.*, 64(2): 748-751 (1998).

Peoples and Sinskey, "Poly-beta-hydroxybutyrate (PHB) biosynthesis in *Alcaligenes eutrophus* H 16. Identification and characterization of the PHB polymerase gene (phbC)", *J Biol Chem.* 264(26):15293-7 (1989).

Peoples and Sinskey, "Fine structural analysis of the *Zoogloea ramigera* phbA-phbB locus encoding beta-ketothiolase and acetoacetyl-CoA reductase: nucleotide sequence of phbB", *Molecular Microbiology*, 3:349-357 (1989).

Peoples and Sinskey, "Poly-beta-hydroxybutyrate biosynthesis in *Alcaligenes eutrophus* H16. Characterization of the genes encoding beta-ketothiolase and acetoacetyl-CoA reductase", *J. Biol. Chem.*, 264:15298-15303 (1989).

Peoples, et al. "Biosynthetic Thiolase from *Zoogloea ramigera*", *J. Biol. Chem.*, 262(1):97-102 (1987).

Peredelchuk and Bennett, "A method for construction of *E. coli* strains with multiple DNA insertions in the chromosome", *Gene*, 187(2):231-238 (1997).

Pieper and Steinbuchel, "Identification, cloning an d sequence analysis of the poly(3-hydroxyalkanoic acid) synthase gene of the gram-positive bacterium *Rhodococcus rubber*", *FEMS Microbiol. Lett.*, 96(1):73-80 (1992).

Poirier, et al., "Polyhydroxybutyrate, a Biodegradable Thermoplastic, Produced in Transgenic Plants", *Science*, 256: 520-523 (1992).

Poirier, et al., "Production of polyhydroxyalkanoates, a family of biodegradable plastics and elastomers, in bacteria and plants", *Biotechnology*, 13(2):142-150 (1995).

Preito, et al., "Engineering of stable recombinant bacteria for production of chiral medium-chain-length poly-3-hydroxyalkanoates", *Appl. Environ. Microbiol.*, 65:3265-3271 (1999).

Qi, et al., "Metabolic routing towards polyhydroxyalkanoic acid synthesis in recombinant *Escherichia coli* (*fad* R): inhibition of fatty acid beta-oxidation by acrylic acid", *FEMS Microbiol. Lett.*, 167(1):89-94 (1998).

Qi, et al., "Production of very long chain polyunsaturated omega-3 and omega-6 fatty acids in plants", *Nature Biotechnology*, 22:739-745 (2004).

Raibaud, et al., "A technique for integrating any DNA fragment into the chromosome of *Escherichia coli*", *Gene*, 29: 231-241 (1984).

Rehm, et al., "A new metabolic link between fatty acid de novo synthesis and polyhydroxyalkanoic acid synthesis. The PHAG gene from *Pseudomonas putida* KT2440 encodes a 3-hydroxyacyl-acyl carrier protein-coenzyme a transferase", J. Biol. Chem., 273:24044-24051 (1998).

Rhie and Dennis, "Role of *fad*R and *ato*C(Con) mutations in poly(3-hydroxybutyrate-co-3-hydroxyvalerate) synthesis in recombinant pha+ *Escherichia coli*", *Appl. Environ. Microbiol.*, 61(7):2487-2492 (1995).

Richards, et al., "Construction of a GFP-BAR plasmid and its use for switchgrass transformation", *Plant Cell Rep.* 20:48-54 (2001).

Roslan, et al., "Characterization of the ethanol-inducible alc gene-expression system in *Arabidopsis thaliana*", *Plant J.* 28:225-235 (2001).

Saito, et al. "An NADP-linked acetoacetyl CoA reductase from *Zoogloea ramigera*", *Arch. Microbiol.*, 114(3):211-17 (1977).

Sambrook, et. al., in *Molecular Cloning, a laboratory manual*, (2nd Ed.), Cold Spring Harbor Laboratory Press:Cold Spring Harbor, NY (1992).

Sato and Hayashi, "Primary Structures of the Genes, *faoA* and *faoB*, from *Pseudomonas fragi* B-0771 Which Encode the Two Subunits of the HDT Multienzyme Complex Involved in Fatty Acid β-Oxidation", *J. Biochem.*, 111:8-15 (1992).

Schembri, et al., "Phosphate concentration regulates transcription of the *Acinetobacter* polyhydroxybutyric acid (PHB) and synthesis of PHB in *Escherichia coli*", *J. Bacteriol.*, 170(12):5837-5847 (1988).

Schena, et al., "A steroid-inducible gene expression system for plant cells", *Proc. Natl. Acad. Sci. USA*, 88:10421-10425 (1991).

Schubert, et al., "Cloning of the *Alcaligenes eutrophus* genes for synthesis of poly-β-hydroxybutyri acid (PHB) and synthesis of PHB in *Escherichia coli*", *J. Bacteriol.*, 170: 5837-5847 (1988).

Sim, et al., "PHA synthase activity controls the molecular weight and polydispersity of polyhydroxybutyrate in vivo", *Nature Biotech.*, 15:63-67 (1997).

Singh, et al., "Nucleotide sequence of a cDNA from *Brassica juncea* encoding a microsomal omega-6-desaturase" (accession No. X91139) (PGR 95-109), *Plant Physiol.*, 109:1498 (1995).

Slater, et al., "Multiple beta-ketothiolases mediate poly(beta-hydroxyalkanoate) copolymer synthesis in *Ralstonia eutropha*", *J. Bacteriol.*, 180(8):1979-87 (1998).

Slater, et al., "Cloning and expression in *Escherichia coli* of the *Alacligenes eutrophus* H16 poly-β-hydroxybutyrate biosynthetic pathway", *J. Bacteriol.*, 170:4431-4436 (1988).

Slater, et al., "Production of poly-(3-hydroxybutyrate-co-3-hydroxyvalerate) in a recombinant *Escherichia coli* strain", *Appl. Environ. Microbiol.*, 58(4):1089-1094 (1992).

Snell and Peoples, "Polyhydroxyalkanoate polymers and their production in transgenic plants", *Metab. Eng.*, 4:29-40 (2002).

Somleva, et al., "*Agrobacterium* -Mediated Genetic Transformation of Switchgrass", *Crop Science*, 42:2080-2087 (2002).

Steinbüchel and Valentin, "Diversity of bacterial polyhydroxyalkanoic acids," *FEMS Microbiol. Lett.* 128:219-28 (1995).

Steinbüchel and Wiese, "A *Pseudomonas* strain accumulating polyesters of 3-hydroxybutyric acid and medium-chain-length 3-hydroxyalkanoic acids", *Appl. Microbiol. Biotechnol.*, 37:691-97 (1992).

Steinbüchel, et al., "Molecular basis for biosynthesis and accumulation of polyhydroxyalkanoic acids in bacteria," *FEMS Microbiol Rev.*, 9(2-4):217-30 (1992).

Sudesh, et al., "Synthesis, structure and properties of polyhydroxyalkanoates: biological polyesters", *Prog. Polym. Sci.*, 25:1503-1555 (2000).

Sweetman, et al., "Ethanol vapor is an efficient inducer of the alc gene expression system in model and crop plant species", *Plant Physiol.*, 129:943-948 (2002).

Tang and Newton, "Regulated gene expression by glucocorticoids in cultured Virginia pine (*Pinus virginiana* Mill.) cells", *J. Exp. Botany*, 55:1499-1508 (2004).

Tang, et al., "Nucleotide sequence of a cDNA clone for Ω-3 fattty acid desaturase from *Aleurites fordii* seeds" ( accession No. AF061027) (PGR 99-009), *Plant Physiol.*, 119:364 (1999).

Timm and Steinbuchel, "Cloning and molecular analysis of the poly(3-hydroxyalkanoic acid) gene locus of *Pseudomonas aeruginosa* PAO1", *Eur. J. Biochem.*, 209:1530 (1992).

Tombolini, et al., "Poly-beta-hydroxybutyrate (PHB) biosynthetic genes in *Rhizobium meliloti* 41", *Microbiology.*, 141 ( Pt 10):2553-9 (1995).

Tominack, "Herbicide formulations", *J Toxicol Clin Toxicol.*, 38(2):129-35 (2000).

Triggs-Raine and Loewen , "Physical characterization of katG, encoding catalase HPI of *Escherichia coli*", *Gene*, 52:121-128 (1987).

Ueda, et al., "Molecular analysis of the poly(3-hydroxyalkanoate) synthase gene from a methylotrophic bacterium, *Paracoccus denitrificans*", *J Bacteriol.*, 178(3):774-9 (1996).

Unger, et al., "A chimeric ecdysone receptor facilitates methoxyfenozide-dependent restoration of male fertility in ms45 maize", *Trans. Res.*, 11:455-465 (2002).

Valentin and Dennis, "Production of poly(3-hydroxybutyrate-co-4-hydroxybutyrate) in recombinant *Escherichia coli* grown on glucose", *J. Biotechnol.*, 58:33-38 (1997).

Valentin, et al., "Identification of 5-hydroxyhexanoic acid, 4-hydroxyaheptanoic acid and 4-hydroxyoctanoic acid as new constituents of bacterial polyhydroxyalkanoic acids", *Appl. Microbiol. Biotechnol.*, 46:261-67 (1996).

Valentin, et al., "Metabolic pathway for biosynthesis of poly(3-hydroxybutyrate-co-4-hydroxybutyrate) from 4-hydroxybutyrate by *Alcaligenes eutrophus*", *Eur. J. Biochem.*, 227:43-60 (1995).

Valentin, et al., "Identification of 4-hydroxyhexanoic acid as a new constituent of biosynthetic polyhydroxyalkanoic acids from bacteria", *Appl. Microbiol. Biotechnol.*, 40:710-16 (1994).

Valentin, et al., "Cloning and characterization of the Methylobacterium extorquens polyhydroxyalkanoic-acid-synthase structural gene", *Appl Microbiol Biotechnol.*, 39(3):309-17 (1993).

Valentin, et al., "Identification of 4-hydroxyvaleric acid as a constituent of biosynthetic polyhydroxyalkanoic acids from bacteria", *Appl. Microbiol. Biotechnol.*, 36: 507-14 (1992).

Wallen and Rohwedder, "Poly-β-hydroxyalkanoate from activated sludge", *Environ. Sci. Technol.*, 8:576-79 (1974).

Wang and Lee, "High cell density culture of metabolically engineered *Escherichia coli* for the production of poly(3-hydroxybutyrate) in a defined medium", *Biotechnol. Bioeng.*, 58(2-3):325-328 (1998).

Wang and Lee, "Production of poly(3-hydroxybutyrate) by fed-batch culture of filamentation suppressed recombinant *Escherichia coli*", *Appl. Environ. Microbiol.*, 63(12):4765-4769 (1997).

Wang, et al., "Chemically regulated ex-pression systems and their applications in transgenic plants" *Trans. Res.*, 12:529-40 (2003).

Wilde, et al., "Control of gene expression in tobacco cells using a bacterial operator-represso r system", *EMBO J.*, 11:1251-1259 (1992).

Williams and Peoples, "Biodegradable plastics from plants," *CHEMTECH*, 26:38-44 (1996).

Yabutani, et al., "Analysis of beta-ketothiolase and acetoacetyl-CoA reductase genes of a methylotrophic bacterium, *Paracoccus denitrificans*, and their expression in *Escherichia coli*", *FEMS Microbiol Lett.*, 133(1-2):85-90 (1995).

Yanisch-Perron, et al., "Improved M13 phage cloning vectors and host strains: nucleotide sequences of the M13mp18 and pUC19 vectors", *Gene*, 33:103-119 (1985).

Ye, et al., "Engineering the provitamin A (beta-carotene) biosynthetic pathway into (carotenoid-free) rice endosperm", *Science*, 287:303-305 (2000).

Yim, et al., "Synthesis of Poly-(3-hydroxybutyrate-co-3-hydroxyvalerate) by recombinant *Escherichia coli*", *Biotech. Bioengineering*, 49:495-503 (1996).

Zhang, et al., "Production of polyhydroxyalkanoates in sucrose-utilizing recombinant *Escherichia coli* and *Klebsiella* strains," *Appl. Environ. Microbiol.*, 60:1198-1205 (1994).

Zuo, et al., "Technical advance: An estrogen receptor-based transactivator XVE mediates highly inducible gene expression in transgenic plants", *Plant J.*, 24:265-273 (2000).

Madi and Prusky, "Sequence of a cDNA clone encoding an avocado (*Persea americana*) [9]-stearoyl-icyl carrier protein desaturase I accession No. AF116861) (PGR 99-167)" *Plant Physiol.*, 121:1057 (1999).

Timm and Steinbuchel, "Cloning and molecular analysis of the poly(3-hydroxyalkanoic acid) gene locus of *Pseudomonas aeruginosa* PA01", *Eur. J. Biochem.*, 209:15-30 (1992).

Valentin, et al., "PHA production, from bacteria to plants", *Int. J. Biol. Macromol.* 25(1-3): 303-306 (1999).

* cited by examiner

SEQUENCE LISTING

<160> NUMBER OF SEQ ID NOS: 6

<210> SEQ ID NO 1
<211> LENGTH: 49
<212> TYPE: DNA
<213> ORGANISM: Artificial Sequence
<220> FEATURE:
<223> OTHER INFORMATION: Primer

<400> SEQUENCE: 1
atttcctctt cagagcagct atgaccatga ttacgccaag cttcgactg          49

<210> SEQ ID NO 2
<211> LENGTH: 47
<212> TYPE: DNA
<213> ORGANISM: Artificial Sequence
<220> FEATURE:
<223> OTHER INFORMATION: Primer

<400> SEQUENCE: 2
tcggtctctt catttcgata cccgatcccc cgtgttctct ccaaatg            47

<210> SEQ ID NO 3
<211> LENGTH: 69
<212> TYPE: DNA
<213> ORGANISM: Artificial Sequence
<220> FEATURE:
<223> OTHER INFORMATION: Primer

<400> SEQUENCE: 3
ttgctctctt caaaaatggc ttctatgata tcctcttccg ctgtgacaac agtcagccgt    60
gcctctagg                                                           69

<210> SEQ ID NO 4

-continued

```
<211> LENGTH: 49
<212> TYPE: DNA
<213> ORGANISM: Artificial Sequence
<220> FEATURE:
<223> OTHER INFORMATION: Primer

<400> SEQUENCE: 4
tggagctctt cactcgagtt aattaattcg aaaagcttgg cactggccg            49

<210> SEQ ID NO 5
<211> LENGTH: 43
<212> TYPE: DNA
<213> ORGANISM: Artificial Sequence
<220> FEATURE:
<223> OTHER INFORMATION: Primer

<400> SEQUENCE: 5
ccttaattaa ctcgaggaat tcatcgattc cgcgggtacc gag                  43

<210> SEQ ID NO 6
<211> LENGTH: 73
<212> TYPE: DNA
<213> ORGANISM: Artificial Sequence
<220> FEATURE:
<223> OTHER INFORMATION: Primer

<400> SEQUENCE: 6
gctctagacc tagggcgcg ccagatctag taacatagat gacaccgcgc gcgataattt  60
atcctagttt gcg                                                   73
```

CHEMICALLY INDUCIBLE EXPRESSION OF BIOSYNTHETIC PATHWAYS

This application claims priority to U.S. provisional application No. 60/662,235 filed Mar. 16, 2005 and to U.S. provisional application Ser. No. 60/669,766 filed Apr. 8, 2005.

FIELD OF THE INVENTION

This invention generally relates to the construction and use of vectors or constructs suitable for achieving chemical induction of two or more genes encoding two or more enzymes in a metabolic pathway in an organism to enhance the production of the desired product of multienzyme pathways of interest. In particular, the construction of such vectors or constructs for the chemically inducible expression of two or more enzymes in the polyhydroxyalkanoate biosynthetic pathways in plants is disclosed. The production of plants using these vectors or constructs and the improved production of the desired product of the multienzyme pathways are also demonstrated.

BACKGROUND OF THE INVENTION

Plant crops are a desirable host for the production of a range of metabolic products including modified vegetable oils, polyhydroxyalkanoates, amino acids, modified lignins, modified starches and nutraceutical products. Very often production of these new products requires the expression of two or more transgenes encoding two or more polypeptides having enzyme activities. It is desirable to be able to express two or more transgenes at a point in the developmental cycle of the plant to maximize the formation of a desired product. In other cases it is desirable to be able to switch on the expression of a metabolic pathway to mitigate negative impacts on plant growth or yield caused by the polypeptides or products of the metabolic pathways.

The development of agricultural systems, in which bioplastics can be produced economically and sustainably in green plants, has the potential to not only dramatically lower the cost of bioplastics, but to sequester $CO_2$.

Polyhydroxyalkanoates (PHAs) are a family of biodegradable biopolymers that can be produced in plants. The desired commercial target of PHA production in plants is 7.5% to 15% dry weight (dwt) (Y. Poirier and K. J. Gruys, in *Biopolyesters*, Y. Doi, A. Steinbuchel Eds. (Wiley-VCH, Weinheim; 2002), pp. 401-435). To date, PHB has been successfully produced in the following plant species: *Arabidopsis thaliana, Brassica napus* and *Zea mays* (C. Nawrath et al. *Proc. Natl. Acad. Sci. USA* 91, 12760 (1994); K. Bohmert et al., *Planta* 211, 841 (2000); K. L. Houmiel, et al., *Planta* 209, 547 (1999); Y. Poirier and K. J. Gruys, in *Biopolyesters*, Y. Doi, A. Steinbuchel Eds. (Wiley-VCH, Weinheim; 2002), pp. 401-435). However, plants producing in excess of 3% dwt PHB often develop a chlorotic phenotype and/or do not achieve full size (Bohmert, K. et al., in *Molecular Biology and Biotechnology of Plant Organelles*. H. Daniell, C. D. Chase Eds. (Kluwer Academic Publishers, Netherlands; 2004, pp. 559-585). These factors resulted in low total polymer yields and represent a major obstacle to the plant-based production of PHA. Attempts to overcome the problem of low total yields using an inducible promoter to control the expression of a single gene in the PHB pathway have yielded high levels of leaky polymer production in un-induced plants such that plants were still stunted (Bohmert et. al. *Plant Physiol.* 128 (4): 1282-90. (2002)).

It is therefore an object of the invention to provide vectors or constructs for the inducible expression of two or more genes encoding two or more enzyme activities in a metabolic pathway in plant crops.

It is a further object of the invention to transform plants with these vectors or constructs and induce the coordinated expression of two or more transgenes encoding two or more enzyme activities required for efficient formation of the desired product in the host plant, such as a biopolymer, a novel oil, a modified lignin, a modified starch or a nutraceutical while limiting detrimental effects that can be associated with constitutive expression of the transgene encoded enzymes in pathways, such as those leading to enhanced formation of the desired product.

It is a still further object of this invention to induce these genes by the foliar or root application of a chemical inducing agent such that the genes are expressed, and the flow of metabolic intermediates is channeled through the appropriate metabolic pathway to enhance the production of a product of that pathway.

It is a further object of this invention to provides methods of application of the chemical inducing agent by foliar or root application at the optimum time during the plant growth cycle to enhance the production of the desired product and to harvest the plant material and recover the product of interest.

BRIEF SUMMARY OF THE INVENTION

Methods and constructs for the introduction of multiple genes encoding enzymes in a multi-enzyme biosynthetic pathway are provided. In one embodiment, the constructs contain two or more enzyme-encoding genes, each under the control of an inducible promoter and each with a polyadenylation signal. The constructs are used to produce transgenic plants, in which the expression of the enzymes is increased when a chemical inducing agent is applied, and a biosynthetic product of the multi-enzyme biosynthetic pathway encoded by the transgenes is produced.

In another embodiment, the method utilizes constructs which contain two or more enzyme-encoding genes under the control of one or more promoters activated by activator molecules or complexes expressed from a transgene or transgenes, which are themselves under the control of one or more inducible promoters and switched on following the external application of a chemical. The transgene or transgenes expressing the activator molecules or complexes may be included in the same construct containing multiple genes encoding enzymes in a multi-enzyme biosynthetic pathway. Alternatively, the transgene or transgenes expressing the activator molecules or complexes may be on a different construct from the construct containing multiple genes encoding enzymes in a multi-enzyme biosynthetic pathway. The activator molecule can be expressed using a constitutive promoter in an inactive form which is converted to the active form following application of the chemical inducing agent.

The biosynthetic pathway may form a number of products including biopolymers, such as a polyhydroxyalkanoates (PHA), vegetable oils containing fatty acids, and nutraceutical compounds. Other biosynthetic pathways include pathways involving the tricarboxylic acid ("TCA") cycle, polyketide synthesis pathway, carotenoid synthesis, glycolysis, gluconeogenesis, starch synthesis, synthesis of lignins and related compounds, production of small molecules that serve as pesticides, fungicides, or antibiotics. The use of inducible promoters to activate transcription of the genes encoding the biosynthetic pathway in a synchronized manner results in the flow of metabolic intermediates to the desired end product at a timepoint optimal for accumulation of that product.

DETAILED DESCRIPTION OF THE INVENTION

Constructs for Transformation of Multiple Genes

Figure 1:
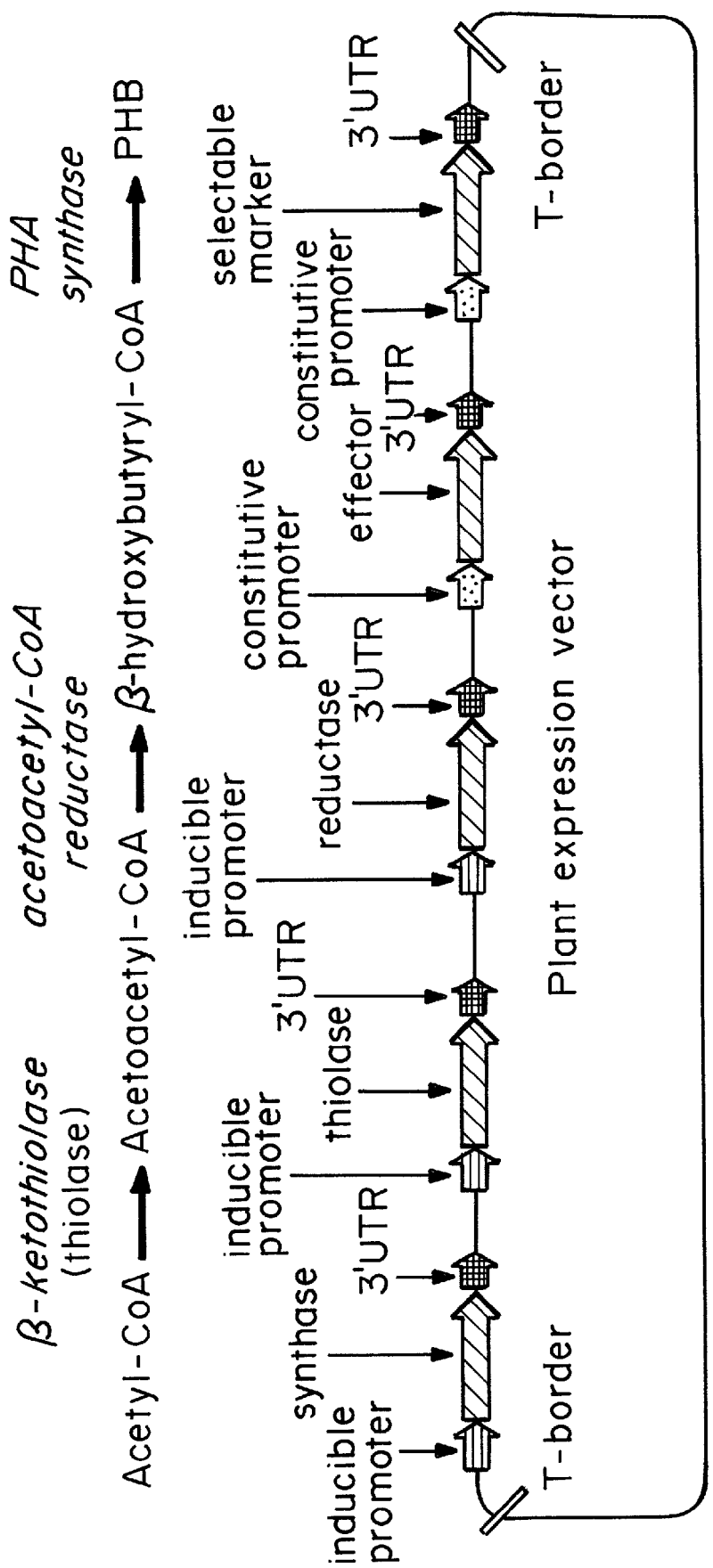
FIG. 1 shows the PHB biosynthetic pathway. In this pathway, acetyl-CoA is converted to acetoacetyl-CoA by a β-ketothiolase. An acetoacetyl-CoA reductase converts acetoacetyl-CoA into β-hydroxybutyryl-CoA. A PHA synthase converts β-hydroxybutyryl-CoA into PHB. A plant expression vector is shown in which all three genes of the PHB biosynthetic pathway are placed under the control of an inducible promoter. These genes are flanked by 3'UTRs. This vector also contains an effector gene under the control of a constitutive promoter flanked by a 3'UTR. This multigene vector also contains a selectable marker under the control of a constitutive promoter and flanked by a 3'UTR.

The constructs may include two or more inducible promoters, the coding regions from two or more genes encoding proteins, and two or more polyadenylation signals. Alternatively, the constructs may contain one or more promoters activated by activator molecules or components of activator molecules, the coding regions from multiple genes encoding proteins, and one or more polyadenylation signals. These constructs can be used in conjunction with constructs containing one or more inducible promoters, the coding regions for one or more genes encoding activator molecules or components of activator molecules, and one or more polyadenylation signals. The constructs may also include sequences encoding targeting sequences, such as sequences encoding plastid targeting sequences, mitochondrial targeting sequences, peroxisomal targeting sequences or tissue specific sequences.

In one embodiment, a construct placing the biosynthetic pathway nucleic acid sequences under the control of multiple inducible promoters preferably contains operatively linked in the 5' to 3' direction, two or more elements, wherein each element contains an inducible promoter that directs transcription of a nucleic acid sequence; a nucleic acid sequence encoding a protein; and a 3' polyadenylation signal sequence.

In another embodiment, a construct placing the biosynthetic pathway nucleic acid sequences under the control of multiple inducible promoters preferably contains a first element including (operatively linked in the 5' to 3' direction): a first inducible promoter that directs transcription of a first nucleic acid sequence encoding a polyhydroxyalkanoate synthase protein; a first nucleic acid sequence encoding a polyhydroxyalkanoate synthase protein; a first 3' polyadenylation signal sequence; a second element including (operatively linked in the 5' to 3' direction): a second inducible promoter that directs transcription of a second nucleic acid sequence encoding an acetoacetyl-CoA reductase protein; a second nucleic acid sequence encoding an acetoacetyl-CoA reductase protein; a second 3' polyadenylation signal sequence; and a third element including (operatively linked in the 5' to 3' direction): a third inducible promoter that directs transcription of a third nucleic acid sequence encoding a beta-ketothiolase protein; a third nucleic acid sequence encoding a beta-ketothiolase protein; and a third 3' polyadenylation signal sequence.

In one embodiment, a construct containing genes expressing multiple enzymes in a biosynthetic pathway includes (operatively linked in the 5' to 3' direction): a promoter activated by an activator molecule or complex that directs transcription of two or more nucleic acid sequences; two or more nucleic acid sequences encoding a protein; and a 3' polyadenylation signal sequence. Alternatively, the construct may contain (operatively linked in the 5' to 3' direction): two or more elements, wherein each element contains a promoter activated by an activator molecule or complex that directs transcription of a nucleic acid sequence; a nucleic acid sequence encoding a protein; and a 3' polyadenylation signal sequence.

These constructs may be used in conjunction with a construct containing (operatively linked in the 5' to 3' direction): an inducible promoter that directs transcription of one or more nucleic acid sequences encoding an activator molecule or complex; one or more nucleic acid sequences encoding an activator molecule or complex; and a 3' polyadenylation signal sequence. Alternatively, the construct may contain (operatively linked in the 5' to 3' direction): two or more elements, wherein each element contains an inducible promoter that directs transcription of a nucleic acid sequence encoding an activator molecule or complex; a nucleic acid sequence encoding an activator molecule or complex; and a 3' polyadenylation signal sequence.

In another embodiment, a construct contains two or more elements, wherein at least one of the elements comprises operatively linked in the 5' to 3' direction: an inducible promoter that directs transcription of one or more nucleic acid sequences encoding an activator molecule or complex; one or more nucleic acid sequences encoding an activator molecule or complex; and a 3' polyadenylation signal sequence; and at least one of the elements comprises operatively linked in the 5' to 3' direction: a promoter activated by an activator molecule or complex that directs transcription of two or more nucleic acid sequence; two or more nucleic acid sequences each encoding a protein; and a 3' polyadenylation signal sequence.

Alternatively, the construct contains three or more elements, wherein at least one of the elements comprises operatively linked in the 5' to 3' direction: an inducible promoter that directs transcription of one or more nucleic acid sequences encoding an activator molecule or complex; one or more nucleic acid sequences encoding an activator molecule or complex; and a 3' polyadenylation signal sequence; and at least two of the elements each comprise operatively linked in the 5' to 3' direction: a promoter activated by an activator molecule or complex that directs transcription of a nucleic acid sequence; a nucleic acid sequence encoding a protein; and a 3' polyadenylation signal sequence.

Production of biosynthetic products in plants can be achieved by transforming the plants with the constructs described above and activating the inducible promoters with any number of agents (described in detail below). Chemical agents can be applied to plants using a number of methods including foliar spray and root drenching.

A. Inducible Promoters and Control of Gene Expression

Inducible promoter systems require the expression of the gene of interest and an effector cassette. The gene of interest is placed under the control of an inducible promoter. The effector cassette consists of a gene encoding the protein responsible for the regulation of the inducible promoter, a transcriptional repressor or activator which is typically expressed under the control of strong constitutive promoter (C. Gatz and I. Lenk, *Trends Plant Sci.* 3: 352 (1998)). A number of chemically-inducible promoters for expression in bacterial, yeast, plant or mammalian cells are known and available.

Promoters and transcription termination sequences may be added to the construct when multiple genes are inserted into an appropriate transformation vector, many of which are commercially available. For example, there are many plant transformation vector options available (Gene Transfer to Plants (1995), Potrykus, I. and Spangenberg, G. eds. Springer-Verlag Berlin Heidelberg New York; "Transgenic Plants: A Production System for Industrial and Pharmaceutical Proteins" (1996), Owen, M. R. L. and Pen, J. eds. John Wiley & Sons Ltd. England and Methods in Plant Molecular biology—a laboratory course manual (1995), Maliga, P., Klessig, D. F., Cashmore, A. R., Gruissem, W. and Varner, J. E. eds. Cold Spring Laboratory Press, New York). In general, plant transformation vectors comprise one or more coding sequences of interest under the transcriptional control of 5' and 3' regulatory sequences, including a promoter, a transcription termination and/or polyadenylation signal and a selectable or screenable marker gene. The usual requirements for 5' regulatory sequences include a promoter, a transcription initiation site, and a RNA processing signal.

Inducible promoter systems used successfully in plants have been extensively reviewed (M. Padidam, *Curr. Opin. Plant Biol.* 6, 169 (2003); R. Wang et al. *Trans. Res.* 12, 529 (2003); C. Gatz and I. Lenk, *Trends Plant Sci.* 3, 352 (1998)). These inducible systems may be activated by chemicals such as tetracycline, pristamycin, pathogen, light, glucocorticoid, estrogen, copper, herbicide safener, ethanol, IPTG (isopropyl β-D-1-thiogalactopyranoside), and pathogens.

In a preferred embodiment, the promoter is activated by ecdysone and ecdysone analogs. Ecdysone inducible promoters contain an ecdysone ligand binding domain (such as that from *Heliothis virescens* Martinez et al., 1999a) fused to a DNA binding domain (for example from another receptor such as the glucocorticoid receptor) and to a transactivating domain (for example the VP16 transactivating domain). Agents which activate ecdysone-inducible promoter include ecdysone, non-steroidal ecdysone analogs such as the biacylhydrazine molecules tebufenozide (active ingredient of the commercial pestide Mimic®), methoxyfenozide (active ingredient of the commercial pesticide Intrepid®), phytoecdysteroids, such as muristerone A and ponasterone A, and insect steroid hormone 20-hydroxyecdysone (Lafont, L. & Dinan, L. *J. Insect Science* 3: 7-95 (2003)). Caged β-ecdysone, which is virtually inactive until it is activated by light, may also be used (Lin et al. *Chemistry & Biology* 9: 1347-1353 (2002)).

Ecdysone-inducible promoters have been successfully used in plants, such as transgenic tobacco (Martinez et al. *Plant J.* 19: 97-106 (1999)); maize suspension cells (Martinez et al. *Mol. Gen. Genet.* 261: 546-552 (1999)); transgenic maize (Unger et al. *Trans. Res.* 11: 455-465 (2002)); and transgenic *Arabidopsis* (Padidam et al. *Current Opinion Plant Biol.* 6: 169-177 (2003); Koo et al. *Plant J.* 37: 439-448 (2004)).

Glucocorticoid-inducible promoters contain a glucocorticoid ligand and DNA binding domain such as that from the human glucocorticoid receptor. Inducing agents include steroidal compounds such as dexamethasone, hydrocortisone, and prednisone. These promoters have been successfully used in plants, such as transgenic tobacco (Aoyama and Chua, *Plant J.* 11: 605-612 (1997); Bohner et al., *Plant J.* 19: 87-95 (1999)); Gremillon et al., *Plant J.* 37: 218-228 (2004)); tobacco suspension cells (Schena et al., *Proc. Natl. Acad. Sci. USA* 88: 10421-10425 (1991)); transgenic *Arabidopsis* (Lloyd et al., *Science* 266: 436-439 (1994)); transgenic rice (Ouwerkerk et al., *Planta* 213: 370-378 (2001)); transgenic *Nicotiana benthamiana* (Mori et al. *Plant J.* 27: 79-86 (2001)); and Virginia pine cell cultures (Tang and Newton, *J. Exp. Botany* 55: 1499-1508 (2004)).

Estrogen-inducible promoters contain the ligand binding domain of an estrogen receptor, typically that of the human estrogen receptor. Inducing agents include β-estradiol. Estrogen inducible promoters have been successfully used in plants, such as transgenic *Arabidopsis* (Zuo et al. *Plant J.* 24: 265-273 (2000)); transgenic tobacco (Zuo et al. *Plant J.* 24: 265-273 (2000)); transgenic *Nicotinia benthamiana* (Guo et al. *Plant J.* 34: 383-392 (2003)); and maize suspension cells (Bruce et al. *Plant Cell* 12: 65-79 (2000)).

Ethanol-inducible promoters are based on the alc regulon of *Aspergillus nidulans*. Ethanol inducible promoters have been successfully used in plants, such as transgenic tobacco (Caddick et al., *Nature Biotechnol.* 16: 177-180 (1998)); Sweetman et al. *Plant Physiol.* 129: 943-948 (2002)), transgenic potato (Sweetman et al., *Plant Physiol.* 129: 943-948 (2002)), transgenic oilseed rape (Sweetman et al., *Plant Physiol.* 129: 943-948 (2002)), transgenic *Arabidopsis* (Roslan et al. *Plant J* 28: 225-235 (2001)).

Herbicide safener-inducible promoters can involve the maize In2-2 promoter. Typical inducing agents include herbicide safeners, such as benzenesulfonamide and sulfonylurea herbicide chlorsulfuron. Herbicide safener inducible promoters have been successfully used in plants (De Veylder et al., *Plant Cell Physiol.* 38: 568-577 (1997) 0.

Copper-inducible promoters are based on the control elements that regulate the expression of copper detoxifying genes in *Saccharomyces cerevisia*. A typical inducing agent is copper sulfate ($CuSO_4$). Copper inducible promoters have been successfully used in plants, such as transgenic tobacco (Mett et al., *Proc. Natl. Acad. Sci. USA* 90: 4567-4571 (1993)).

Tetracycline-inducible promoters can consist of elements of the tetracycline resistance operon from *E. coli*. These promoters can be used as an activator or a repressor and in combination with other inducible systems to achieve dual control. For example, the tet inducible repressor system can be combined with the glucocorticoid inducible system to obtain a tightly controlled on/off switch (Bohner et al., *Plant J.* 19: 87-95 (1999)). The tetracycline-responsive promoter/tetracycline-controlled transactivator (tTA) system is well known in the art (Gossen M and Bujard H *Proc Natl Acad Sci USA* 89: 5547-5551 (1992); Adams et al. *Mol. Pharmacol.* 55(6); 1028-1036 (1999)). Tetracycline inducible promoters have been successfully used in plants, such as transgenic tobacco (Bohner et al., *Plant J.* 19: 87-95 (1999)) and tobacco protoplasts (Gatz and Quail, Proc. Natl. Acad. Sci. USA 85: 1394-1397 (1988)).

Pristamycin-inducible promoters are based on the transcriptional activator (PIT) which consists of the PIP protein, the repressor of the pristamycin operon of *S. coelicolor*. Inducing agents include the streptogramin antibiotic pristamycin. Pristamycin inducible promoters have been successfully used in plants, such as tobacco suspension cells (Frey et al., *Biotechnol. & Bioengineering* 74: 154-163 (2001)).

Pathogen-inducible promoters can involve the Prp1-a promoter from potato. Inducing agents include pathogen attack, but the promoters respond to chemicals such as benothiadiazole (BTH) and salicylic acid. Pathogen inducible promoters have been successfully used in plants, such as *Arabidopsis* and tobacco (Bohmert et al., *Plant Physiol.* 128: 1282-1290 (2002)).

Isopropyl β-D-1-thiogalactopyranoside (IPTG) is a synthetic, nonhydrolyzable inducer of the *E. coli* lac repressor. Studies have demonstrated that IPTG can be used in cells to induce the expression of host cell genes controlled by the lac repressor/operator system (Wilde et al., *EMBO J.* 11, 1251-1259 (1992); Itzhaki et al. *Nat. Genet.* 15:258-265 (1997)).

Induction of the promoters can be optimized by enhancing efficacy of the inducing agent either by increasing stability and/or uptake of the inducing agent or by increasing the affinity of the inducing agent for the ligand binding domain of the inducible promoter. Chemical modification of the structure of the inducing agent and/or formulation of the solution containing the inducing agent could be used to achieve these goals.

The inducible promoters could be optimized through gene shuffling techniques to enhance the ligand and/or DNA binding domains and/or the minimal promoter to improve the inducibility of the system.

Plant promoters can be selected to control the expression of the transgene in different plant tissues or organelles for all of which methods are known to those skilled in the art (Gasser & Fraley, Science 244:1293-99 (1989)). The 5' end of the transgene may be engineered to include sequences encoding plastid or other subcellular organelle targeting peptides, such as a plastid targeting signal, linked in-frame with the transgene.

B. Enzymes in Biosynthetic Pathways

Methods and constructs for the introduction of multiple genes encoding enzymes in a multi-enzyme biosynthetic pathway are provided.

In one embodiment, the constructs contain inducible promoters driving the expression of multiple gene sequences, each encoding a different protein within a biosynthetic pathway. The constructs contain an effector cassette consisting of a gene encoding the protein responsible for the regulation. This gene has a polyadenylation signal, and is typically placed under the control of strong constitutive or tissue specific promoter. The constructs contain two or more, for example, 2-12, preferably 2-8, and more preferably, 2-7, enzyme-encoding genes, each under the control of an inducible promoter and each having a polyadenylation signal, and are used to produce transgenic organisms in which the expression of the enzymes are increased when the chemical inducing agent is applied, and the product of the series of enzymes encoded by the trangenes is produced. An illustration of such a construct using the PHB biosynthetic pathway as an example is presented in FIG. 1.

In a preferred embodiment, the products of the transgenes are enzymes and other factors required for production of a biopolymer, such as a polyhydroxyalkanoate (PHA), a vegetable oil containing fatty acids with a desirable industrial or nutritional profile, or a nutraceutical compound.

Where the product is a PHA, it may be a homopolymer or copolymer of 3-hydroxybutyrate. In this case the transgenes can encode enzymes selected from beta-ketothiolase, acetoacetyl-CoA reductase, PHB ("short chain") synthase, PHA ("long chain") synthase, threonine dehydratase, dehydratase, isomerase, propionyl-CoA synthetase, hydroxyacyl-CoA synthetase, hydroxyacyl-CoA transferase, thioesterase, fatty acid synthesis enzymes and fatty acid beta-oxidation enzymes. Useful genes are well known in the art, and are disclosed for example by Snell and Peoples *Metab. Eng.* 4: 29-40 (2002) and Bohmert et. al. in *Molecular Biology and Biotechnology of Plant Organelles*. H. Daniell, C. D. Chase Eds. (Kluwer Academic Publishers, Netherlands; 2004, pp. 559-585), and outlined in FIGS. 2 and 3.

Examples of PHA synthases include a synthase with medium chain length substrate specificity, such as phaC1 from *Pseudomonas oleovorans* (WO 91/00917; Huisman, et al. *J. Biol. Chem.* 266, 2191-2198 (1991)) or *Pseudomonas aeruginosa* (Timm, A. & Steinbuchel, A. *Eur. J. Biochem.* 209: 15-30 (1992)), the synthase from *Alcaligenes eutrophus* with short chain length specificity (Peoples, O. P. & Sinskey, A. J. *J. Biol. Chem.* 264:15298-15303 (1989)), or a two subunit synthase such as the synthase from *Thiocapsa pfennigii* encoded by phaE and phaC (U.S. Pat. No. 6,011,144). Other useful PHA synthase genes have been isolated from, for example, *Aeromonas caviae*(Fukui & Doi, *J. Bacteriol.* 179: 4821-30 (1997)), *Rhodospirillum rubrum* (U.S. Pat. No. 5,849,894), *Rhodococcus ruber* (Pieper & Steinbuechel, *FEMS Microbiol. Lett.* 96(1): 73-80 (1992)), and *Nocardia corallina* (Hall et. al., *Can. J. Microbiol.* 44: 687-91 (1998)). PHA synthases with broad substrate specificity useful for producing copolymers of 3-hydroxybutyrate and longer chain length (from 6 to 14 carbon atoms) hydroxyacids have also been isolated from *Pseudomonas* sp. A33 (Appl. Microbiol. Biotechnol. 42: 901-909 (1995)) and *Pseudomonas* sp. 61-3 (Kato, et al. Appl. Microbiol. Biotechnol. 45: 363-370 (1996)).

A range of PHA synthase genes and genes encoding additional metabolic steps useful in PHA biosynthesis are described by Madison and Huisman. *Microbiology and Molecular biology Reviews* 63:21-53 (1999)).

Figure 2:
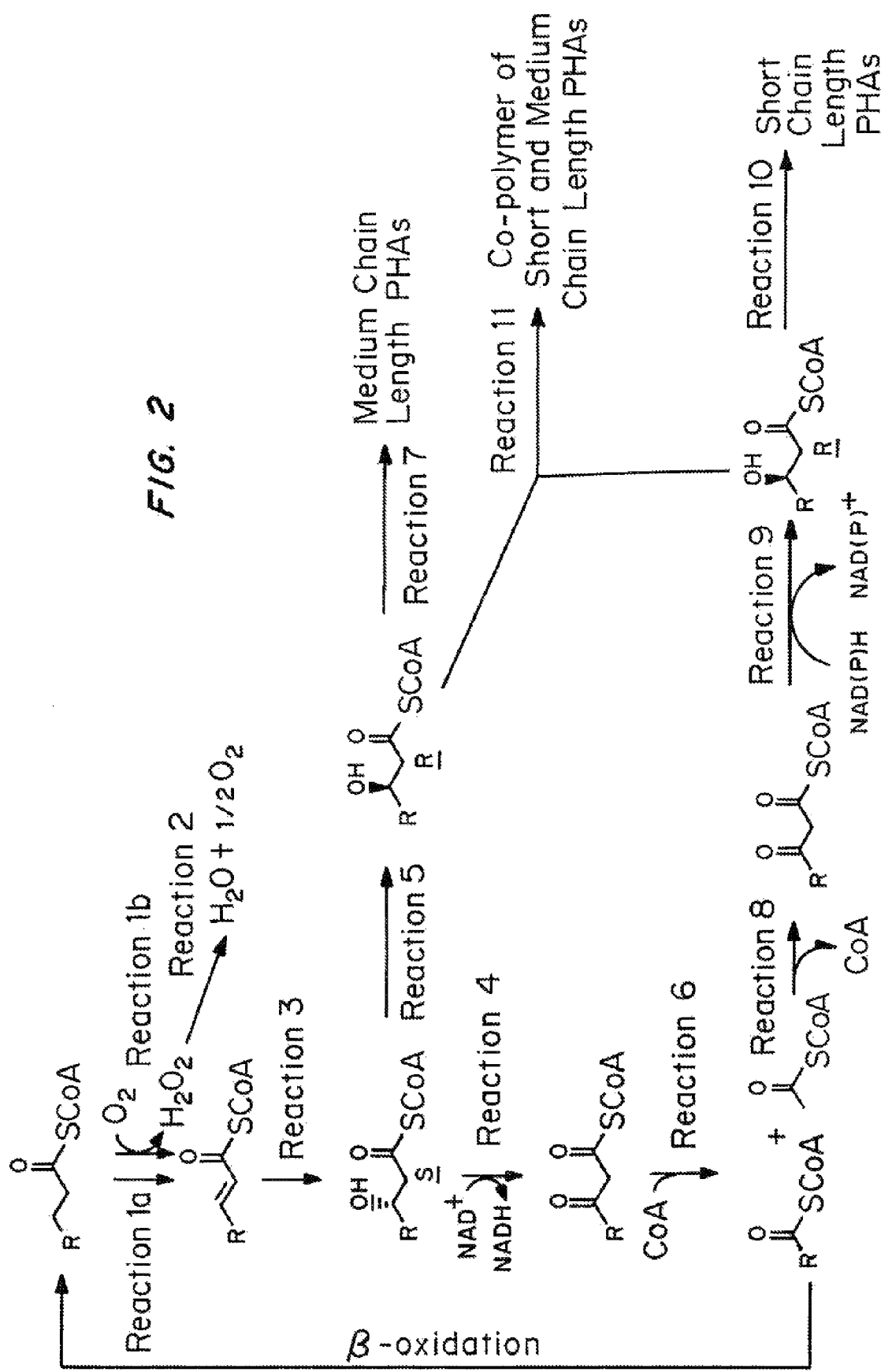
FIG. 2 shows routes for short and medium chain length PHA production from fatty acid degradation (also known as fatty acid beta-oxidation) pathways. Activities to promote PHA synthesis from fatty acid degradation can be selected from the following: acyl CoA dehydrogenases (Reaction 1 a), acyl CoA oxidases (Reaction 1 b), catalases (Reaction 2), alpha subunits of beta-oxidation (Reactions 3, 4, 5), beta subunits of beta-oxidation (Reaction 6), PHA synthases with medium chain length substrate specificity (Reaction 7), beta-ketothiolases (Reaction 8), NADH or NADPH dependent reductases (Reaction 9), PHA synthases with short chain length specificity (Reaction 10), and PHA synthases that incorporate both short and medium chain length substrates (Reaction 11). Selected activities can be produced in the host plant by transformation of the appropriate genetic construct(s).

An alpha subunit of beta-oxidation pertains to a multifunctional enzyme that minimally possesses hydratase and dehydrogenase activities (FIG. 2). The subunit may also possess epimerase and Δ3-cis, Δ2-trans isomerase activities. Examples of alpha subunits of beta-oxidation are FadB from *E. coli*(DiRusso, C. C. J. Bacteriol. 1990, 172, 6459-6468), FaoA from *Pseudomonas fragi* (Sato, S., Hayashi, et al. J. Biochem. 1992, 111, 8-15), and the *E. coli* open reading frame f714 that contains homology to multifunctional α subunits of β-oxidation (Genbank Accession # 1788682). A β subunit of β-oxidation refers to a polypeptide capable of forming a multifunctional enzyme complex with its partner α subunit. The β subunit possesses thiolase activity (FIG. 2). Examples of β subunits are FadA from *E. coli* (DiRusso, C. C. *J. Bacteriol.* 172: 6459-6468 (1990)), FaoB from *Pseudomonas fragi* (Sato, S., Hayashi, M., Imamura, S., Ozeki, Y., Kawaguchi, A. *J. Biochem.* 111: 8-15 (1992)), and the *E. coli* open reading frame f436 that contains homology to α subunits of β-oxidation (Genbank Accession # AE000322; gene b2342).

A reductase refers to an enzyme that can reduce β-ketoacyl CoAs to R-3-OH-acyl CoAs, such as the NADH dependent reductase from *Chromatium vinosum* (Liebergesell, M., & Steinbuchel, A. *Eur. J. Biochem.* 209: 135-150 (1992)), the NADPH dependent reductase from *Alcaligenes eutrophus* (Peoples, O. P. & Sinskey, A. J. *J. Biol. Chem.* 264: 15293-15297 (1989))), the NADPH reductase from *Zoogloea ramigera* (Peoples, O. P. & Sinskey, A. J. Molecular Microbiology 3: 349-357 (1989)) or the NADPH reductase from *Bacillus megaterium* (U.S. Pat. No. 6,835,820).

A beta-ketothiolase refers to an enzyme that can catalyze the conversion of acetyl CoA and an acyl CoA to a α-ketoacyl CoA, a reaction that is reversible (FIG. 2). An example of such thiolases are PhaA from *Alcaligenes eutropus* (Peoples, O. P. & Sinskey, A. J. J. Biol. Chem. 264: 15293-15297 (1989)), and BktB from *Alcaligenes eutrophus* (Slater et al. *J. Bacteriol.* 180(8):1979-87 (1998)). An acyl CoA oxidase refers to an enzyme capable of converting saturated acyl CoAs to Δ 2 unsaturated acyl CoAs (FIG. 2). Examples of acyl CoA oxidases are POX1 from *Saccharomyces cerevisiae* (Dmochowska, et al. *Gene*, 1990, 88, 247-252) and ACX1 from *Arabidopsis thaliana* (Genbank Accession # AF057044). A catalase refers to an enzyme capable of converting hydrogen peroxide to hydrogen and oxygen. Examples of catalases are KatB from *Pseudomonas aeruginosa* (Brown, et al. *J. Bacteriol.* 177: 6536-6544 (1995)) and KatG from *E. coli* (Triggs-Raine, B. L. & Loewen, P. C. Gene 52: 121-128 (1987)).

Figure 4:
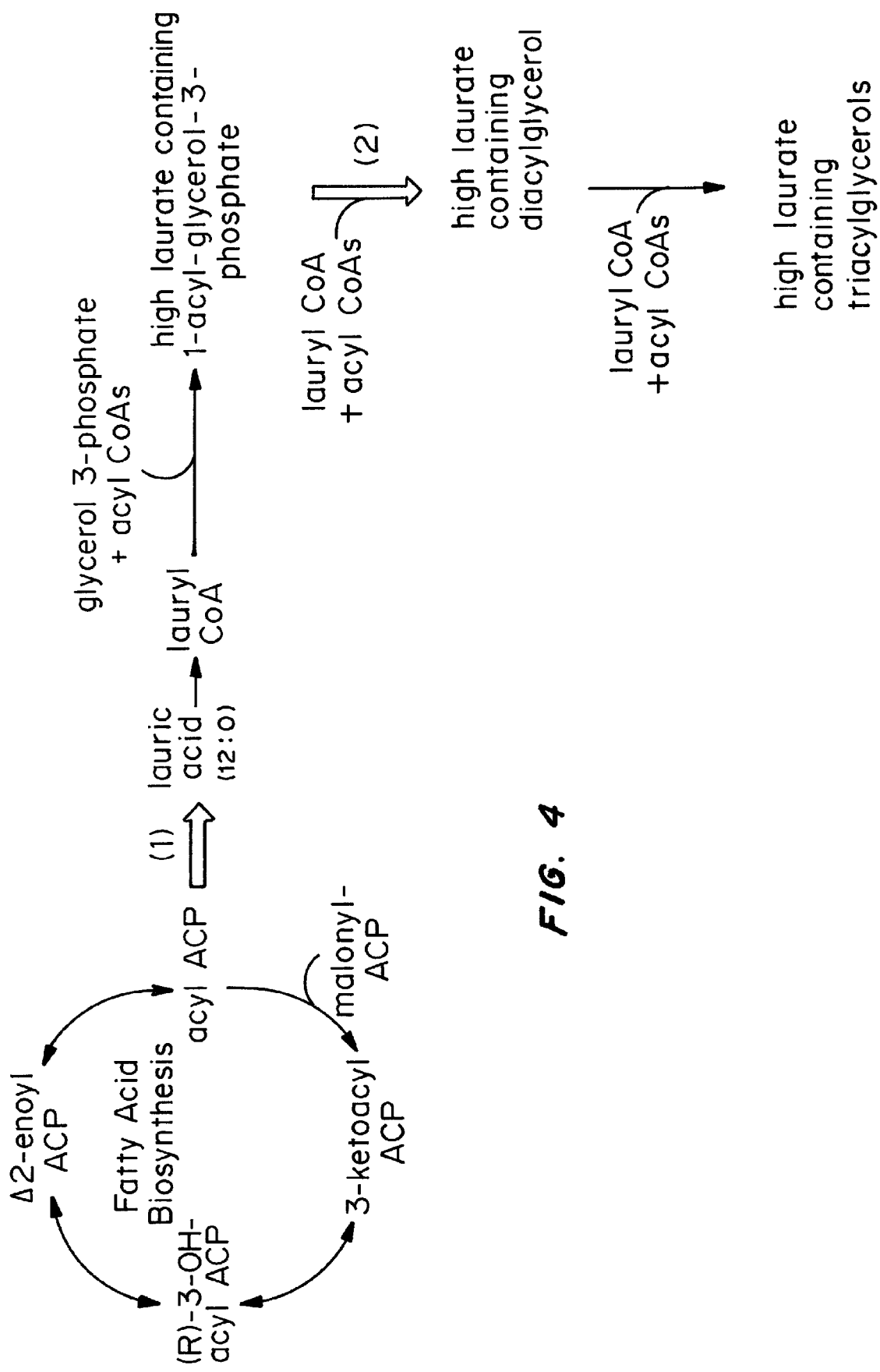
FIG. 4 is a schematic pathway for production of high laurate containing oilseeds. Activities to promote increased laurate content in oils can be selected from the following: 12:0-acyl-carrier protein thioesterases (Reaction 1) and 12:0-coenzyme A preferring lysophosphatitic acid acyl transferases (reaction 2). Selected activities can be produced in the host plant by transformation of the appropriate genetic construct(s).
Figure 5B:
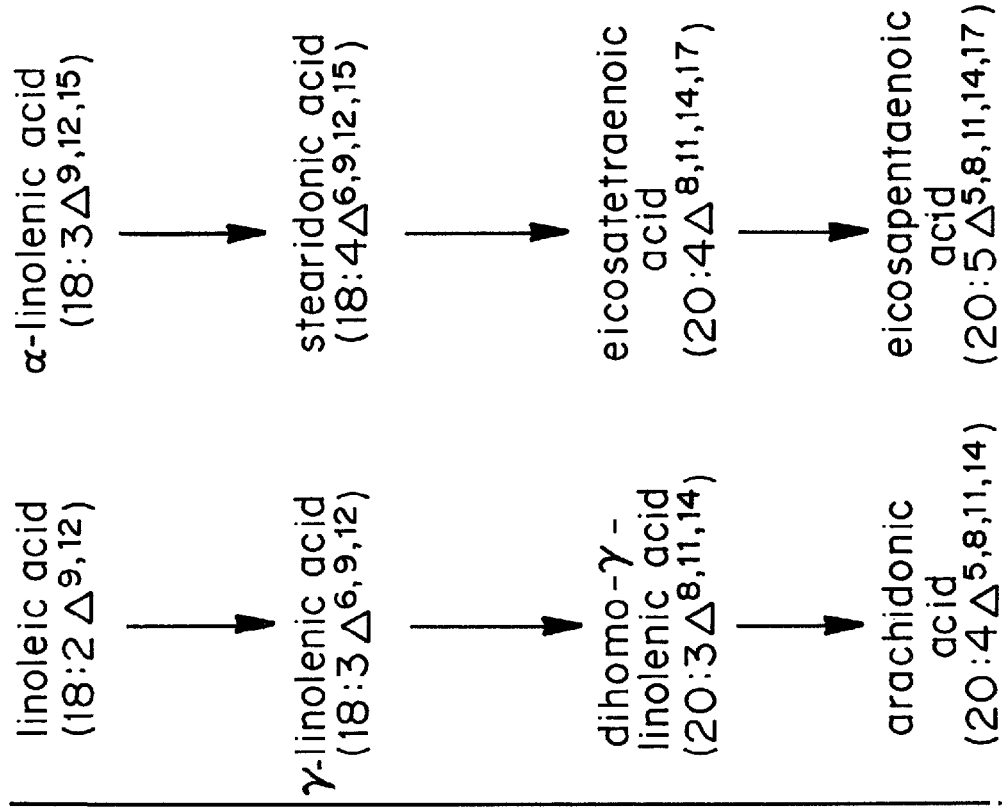
FIG. 5 shows pathways for production of very long chain polyunsaturated fatty acids in plants. Activities to promote the synthesis of these fatty acids in plants can be selected from the following: $\Delta^9$-elongase (Reaction 1), $\Delta^8$-desaturase (Reaction 2). $\Delta^5$ desaturase (Reaction 3), Δ6-desaturase (Reaction 4), and $\Delta^6$-elongase (Reaction 5). Selected activities can be produced in the host plant by transformation of the appropriate genetic construct(s).
Figure 5A:
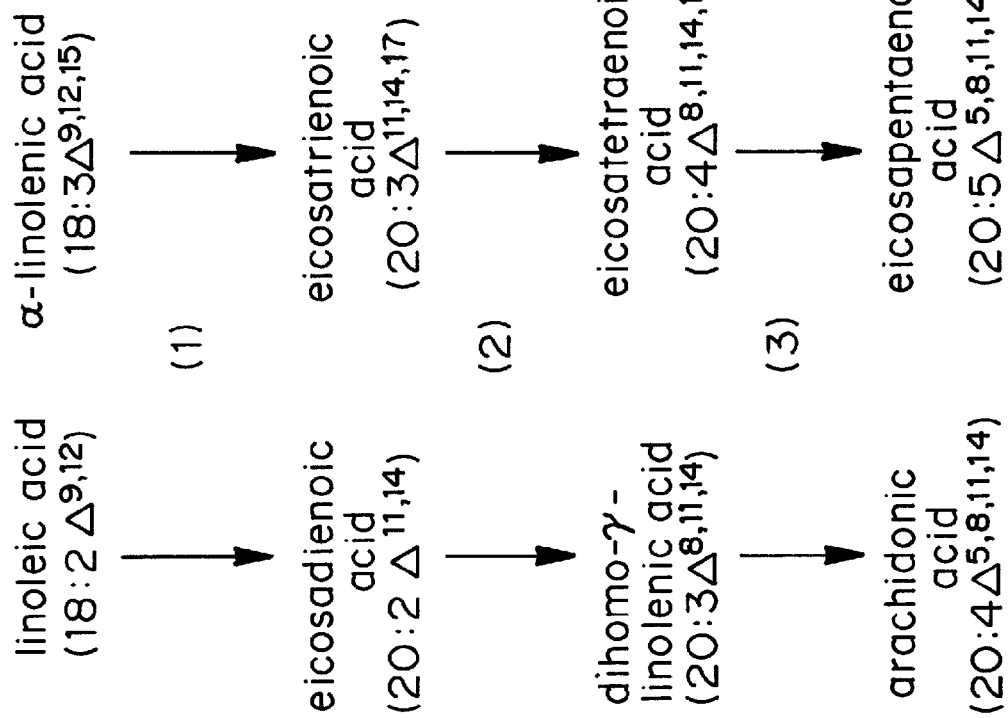

In the case where the product of the transgene encoded enzymes is a modified oil, the transgenes can encode enzymes selected from thioesterase, delta-9-desaturase, omega-3-desaturase, omega-6-desaturase, fatty acid elongase, hydroxylase, and/or triacyl-glycerol biosynthesis enzymes. These enzymes are disclosed in a number of references including U.S. Pat. No. 6,140,486; U.S. Pat. No. 5,955,650; U.S. Pat. No. 6,433,250; U.S. Pat. No. 6,051,754; U.S. Pat. No. 6,635,451; Singh et al. *Plant Physiol.* 109: 1498 (1995); Tang et al. *Plant Physiol.* 119: 364 (1999); and Madi and Prusky *Plant Physiol.* 121: 1057 (1999)). The vegetable oil product may have an improved fatty acid composition for industrial use, for example, a high hydroxyacid content, a high oleic acid content, or a higher or lower unsaturated fatty acid content. Genes and systems for increasing the lauric acid content of rapeseed oil have been described by Knutzon et al. (1999, *Plant Physiol.* 120, 739-746) and are shown in FIG. 4. Where the vegetable oil product has enhanced nutritional properties, it may have a reduced unsaturated fatty acid content, for example, high oleic acid or lauric acid content or an enhanced level of long chain polyunsaturated fatty acids (PUFAs). Genes and systems for increasing the level of PUFAs in an oilseed are described by Qi et al. *Nature Biotechnology* 22:739-745 (2004)) and are outlined in FIG. 5. Additional metabolic engineering strategies for production of new oilseed crops are reviewed by Drexler et al. *J Plant Physiol* 160: 779-802 (2003)).

Figure 6:
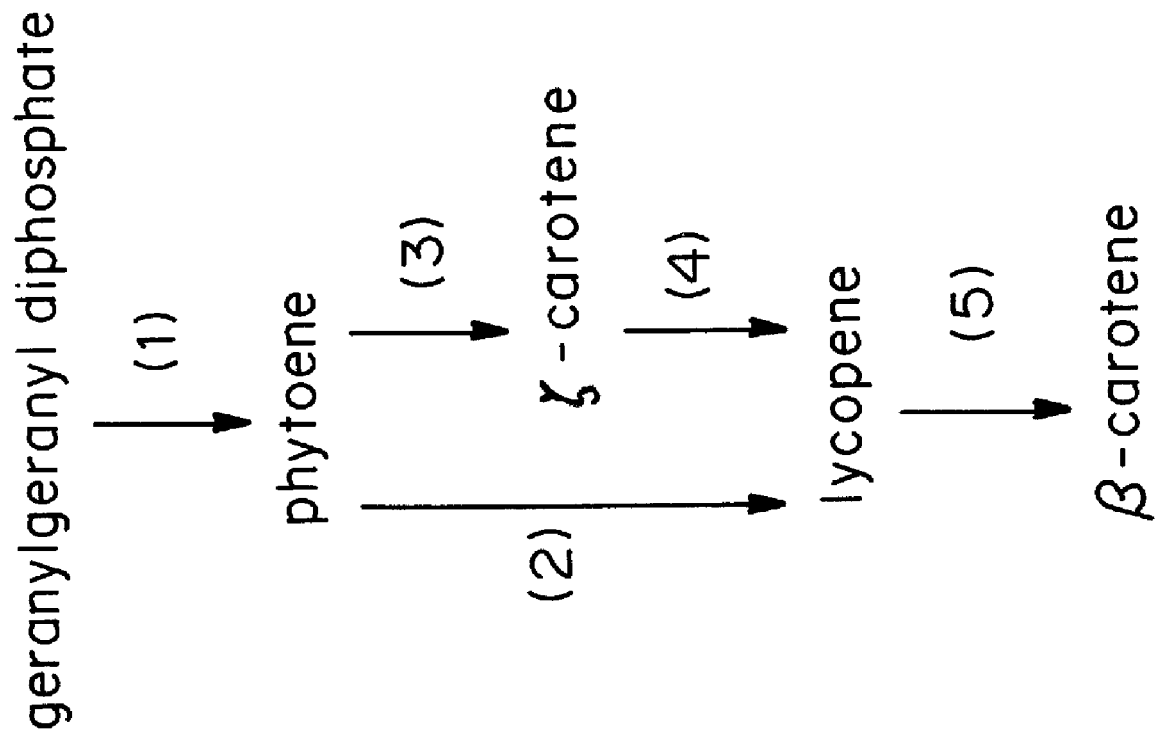
FIG. 6 is a schematic pathway for β-carotene (provitamin A) production in transgenic plants. Activities to promote β-carotene formation from the endogenous plant intermediate geranylgeranyl diphosphate can be selected from the following: phytoene synthase (Reaction 1), carotene desaturase capable of converting phytoene to lycopene (Reaction 2), phytoene desaturase (Reaction 3), ζ-carotene desaturase (Reaction 4), and lycopene β-cyclase (Reaction 5). Selected activities can be produced in the host plant by transformation of the appropriate genetic construct(s).

The product of the transgene encoded enzymes can also be a nutraceutical compound, such as β-carotene (provitamin A). Genes and systems for producing β-carotene in transgenic rice are described by Ye et al. *Science* 287: 303-305 (2000)) and are outlined in FIG. 6. Transgenes within the inducible expression cassettes can encode enzyme activities selected from reactions 1-5 in FIG. 6.

C. Targeting Sequences

Transgenes encoding multiple enzyme reactions may encode a native multienzyme complex, for example, a microbial fatty acid oxidation complex or a bifunctional enzyme encoding amino acid pathway enzyme activities, such as the *Escherichia coli* homoserine dehydrogenase-aspartokinase involved in threonine production. Many examples of such genes encoding multifunctional enzymes exist in the literature. In other cases a transgene may be constructed to encode a multifunctional enzyme through gene fusion techniques in which the coding sequences of different genes are fused with or without linker sequences to obtain a single gene encoding a single protein with the activities of the individual genes. Such synthetic fusion gene/enzyme combinations can be further optimized using molecular evolution technologies.

In another embodiment, constructs containing multiple genes encoding enzymes in a multi-enzyme biosynthetic pathway are placed under the control of one or more promoters which are activated by an activator molecule or complex expressed from a transgene or transgenes, which are under the control of one or more inducible promoters and are switched on following external application of a chemical. In this situation, the transgenic organism is treated with a chemical inducing agent that increases the expression of an activator molecule or a component of the activator molecule, which is then able to increase the expression of the transgenes encoding the multi-enzyme activities at a time optimal for the production of the metabolic product.

In both embodiments, the induction is ideally carried out at a time in the growth cycle of the plant to enhance the level of the desired product. Preferably, the chemical inducing agent is applied as a foliar spray (Tominack. *J Toxicol Clin Toxicol.* 38(2):129-35 (2000)), although root drenching is a useful alternative (Holt et al. *Planta.* 196(2):295-302 (1995)). The metabolic product may be produced in any part of the plant, for example, leaves, stems, flowers, seeds or any combination thereof.

The heterologous nucleotide sequence may further include, within the region that encodes the enzyme to be expressed, one or more nucleotide sequences comprising a targeting sequence. A "targeting" sequence is a nucleotide sequence that encodes, as part of the enzyme, an amino acid sequence or motif that directs the protein to a particular cellular compartment, resulting in localization or compartmentalization of the protein. Presence of a targeting amino acid sequence in a protein typically results in translocation of all or part of the targeted protein across an organelle membrane and into the organelle interior. Alternatively, it may direct the targeted protein to remain embedded in the organelle membrane. The "targeting" sequence or region of a targeted protein may comprise a string of contiguous amino acids or a group of noncontiguous amino acids. The targeting sequence can be selected to direct the targeted protein to a plant organelle such as a nucleus, a microbody (e.g., a peroxisome, or a specialized version thereof, such as a glyoxysome) an endoplasmic reticulum, an endosome, a vacuole, a plasma membrane, a cell wall, a mitochondria, a chloroplast or a plastid.

A chloroplast targeting sequence is any peptide sequence that can target a protein to the chloroplasts or plastids, such as the transit peptide of the small subunit of the alfalfa ribulose-biphosphate carboxylase (Khoudi, et al., Gene 1997, 197, 343-351). A peroxisomal targeting sequence refers to any peptide sequence, either N-terminal, internal, or C-terminal, that can target a protein to the peroxisomes, such as the plant C-terminal targeting tripeptide SKL (Banjoko, A. & Trelease, R. N. Plant Physiol. 1995, 107, 1201-1208; T. P. Wallace et al., "Plant Organellular Targeting Sequences," in Plant Molecular Biology, Ed. R. Croy, BIOS Scientific Publishers Limited (1993) pp. 287-288, and peroxisomal targeting in plant is shown in M. Volokita, The Plant J., 361-366 (1991)).

D. Marker Genes

Selectable marker genes for use in plants include the neomycin phosphotransferase gene nptII (U.S. Pat. No. 5,034,322, U.S. Pat. No. 5,530,196), hygromycin resistance gene (U.S. Pat. No. 5,668,298), and the bar gene encoding resistance to phosphinothricin (U.S. Pat. No. 5,276,268). EP 0 530 129 A1 describes a positive selection system which enables the transformed plants to outgrow the non-transformed lines by expressing a transgene encoding an enzyme that activates an inactive compound added to the growth media. U.S. Pat. No. 5,767,378 describes the use of mannose or xylose for the positive selection of transgenic plants. Screenable marker genes include the beta-glucuronidase gene (Jefferson et al., 1987, EMBO J. 6: 3901-3907; U.S. Pat. No. 5,268,463) and native or modified green fluorescent protein gene (Cubitt et al., 1995, Trends Biochem Sci. 20: 448-455; Pan et al., 1996, Plant Physiol. 112: 893-900). Some of these markers have the added advantage of introducing a trait e.g. herbicide resistance, into the plant of interest providing an additional agronomic value on the input side.

E. Transcription Termination Sequences

At the extreme 3' end of the transcript, a polyadenylation signal can be engineered. A polyadenylation signal refers to any sequence that can result in polyadenylation of the mRNA in the nucleus prior to export of the mRNA to the cytosol, such as the 3' region of nopaline synthase (Bevan, M., Barnes, W. M., Chilton, M. D. Nucleic Acids Res. 1983, 11, 369-385).

II. Methods for Using Constructs

A. Transformation

DNA constructs useful in the methods described herein include transformation vectors capable of introducing transgenes into plants. As used herein, "transgenic" refers to an organism in which a nucleic acid fragment containing a heterologous nucleotide sequence has been introduced. The transgenes in the transgenic organism are preferably stable and inheritable. The heterologous nucleic acid fragment may or may not be integrated into the host genome.

Several plant transformation vector options are available, including those described in "Gene Transfer to Plants" (Potrykus, et al., eds.) Springer-Verlag Berlin Heidelberg New York (1995); "Transgenic Plants: A Production System for Industrial and Pharmaceutical Proteins" (Owen, et al., eds.) John Wiley & Sons Ltd. England (1996); and "Methods in Plant Molecular Biology: A Laboratory Course Manual" (Maliga, et al. eds.) Cold Spring Laboratory Press, New York (1995). Plant transformation vectors generally include one or more coding sequences of interest under the transcriptional control of 5' and 3' regulatory sequences, including a promoter, a transcription termination and/or polyadenylation signal, and a selectable or screenable marker gene. For the expression of two or more polypeptides from a single transcript, additional RNA processing signals and ribozyme sequences can be engineered into the construct (U.S. Pat. No. 5,519,164). This approach has the advantage of locating multiple transgenes in a single locus, which is advantageous in subsequent plant breeding efforts. An additional approach is to use a vector to specifically transform the plant plastid chromosome by homologous recombination (U.S. Pat. No. 5,545,818), in which case it is possible to take advantage of the prokaryotic nature of the plastid genome and insert a number of transgenes as an operon.

The transformation of suitable agronomic plant hosts using these vectors can be accomplished with a variety of methods and plant tissues. Representative plants useful in the methods disclosed herein include the *Brassica* family including *napus, rappa,* sp. *carinata* and *juncea; Arabidopsis thaliana;* maize; soybean; cottonseed; sunflower; palm; coconut; safflower; peanut; mustards including Sinapis alba; sugarcane and flax. Crops harvested as biomass, such as silage corn, alfalfa, switchgrass, sorghum or tobacco, also are useful with the methods disclosed herein. Representative tissues for transformation using these vectors include protoplasts, cells, callus tissue, leaf discs, pollen, and meristems. Representative transformation procedures include *Agrobacterium*-mediated transformation, biolistics, microinjection, electroporation, polyethylene glycol-mediated protoplast transformation, liposome-mediated transformation, and silicon fiber-mediated transformation (U.S. Pat. No. 5,464,765; "Gene Transfer to Plants" (Potrykus, et al., eds.) Springer-Verlag Berlin Heidelberg New York (1995); "Transgenic Plants: A Production System for Industrial and Pharmaceutical Proteins" (Owen, et al., eds.) John Wiley & Sons Ltd. England (1996); and "Methods in Plant Molecular Biology: A Laboratory Course Manual" (Maliga, et al. eds.) Cold Spring Laboratory Press, New York (1995)).

Soybean can be transformed by a number of reported procedures (U.S. Pat. Nos. 5,015,580; 5,015,944; 5,024,944; 5,322,783; 5,416,011; 5,169,770).

A number of transformation procedures have been reported for the production of transgenic maize plants including pollen transformation (U.S. Pat. No. 5,629,183), silicon fiber-mediated transformation (U.S. Pat. No. 5,464,765), electroporation of protoplasts (U.S. Pat. Nos. 5,231,019; 5,472,869; 5,384,253), gene gun (U.S. Pat. Nos. 5,538,877;

5,538,880), and *Agrobacterium*-mediated transformation (EP 0 604 662 A1; WO 94/00977). The *Agrobacterium*-mediated procedure is particularly preferred as single integration events of the transgene constructs are more readily obtained using this procedure which greatly facilitates subsequent plant breeding. Cotton can be transformed by particle bombardment (U.S. Pat. No. 5,004,863; U.S. Pat. No. 5,159,135). Sunflower can be transformed using a combination of particle bombardment and *Agrobacterium* infection (EP 0 486 233 A2; U.S. Pat. No. 5,030,572). Flax can be transformed by either particle bombardment or *Agrobacterium*-mediated transformation. Switchgrass can be transformed using either biolistic or *Agrobacterium* mediated methods (Richards et al. *Plant Cell Rep.* 20: 48-54 (2001); Somleva et al. *Crop Science* 42: 2080-2087 (2002)). Methods for sugarcane transformation have also been described (Franks & Birch *Aust. J Plant Physiol.* 18, 471-480 (1991); PCT WO 2002/037951).

Recombinase technologies which are useful in practicing the current invention include the cre-lox, FLP/FRT and Gin systems. Methods by which these technologies can be used for the purpose described herein are described for example in (U.S. Pat. No. 5,527,695; Dale And Ow, 1991, Proc. Natl. Acad. Sci. USA 88: 10558-10562; Medberry et al., 1995, Nucleic Acids Res. 23: 485-490).

Following transformation by any one of the methods described above, the following procedures can be used to obtain a transformed plant expressing the transgenes: select the plant cells that have been transformed on a selective medium; regenerate the plant cells that have been transformed to produce differentiated plants; select transformed plants expressing the transgene producing the desired level of desired polypeptide(s) in the desired tissue and cellular location.

B. Production of Biosynthetic Products

The expression of multiple enzymes is useful for altering the metabolism of plants to increase, for example, the levels of nutritional amino acids (Falco et. al. *Biotechnology* 13: 577 (1995)), to modify lignin metabolism (Baucher et al. *Crit. Rev. Biochem. Mol. Biol.* 38: 305-350 (2003)), to modify oil compositions (Drexler et al. *J Plant Physiol.* 160: 779-802 (2003)), to modify starch, or to produce polyhydroxyalkanoate polymers (Huisman and Madison, *Microbiol and Mol. Biol. Rev.* 63: 21-53 (1999); and references therein). In preferred embodiments, the product of the transgenes is a biopolymer, such as a polyhydroxyalknaoate (PHA), a vegetable oil containing fatty acids with a desirable industrial or nutritional profile, or a nutraceutical compound.

Production of PHA Biopolymers

Modification of plants to produce PHA biopolymers is a preferred example of how these constructs can be used. The PHA biopolymers encompass a broad class of polyesters with different monomer compositions and a wide range of physical properties (Madison and Huisman, 1999; Dudesh et al. *Prog. Polym. Sci.* 25: 1503-1555 (2000)). Short chain, medium chain, as well as copolymers of short and medium chain length PHAs, can be produced in plants by manipulating the plant's natural metabolism to produce 3-hydroxyacyl CoAs, the substrate of the PHA synthase, in the organelle in which polymer is to be accumulated. This often requires the expression of two or more recombinant proteins, with an appropriate organelle targeting signal attached. The proteins can be coordinately expressed from a single construct introduced into the plant via a single transformation event. In general, a PHA is formed by polymerization (e.g., enzymatic polymerization) of one or more monomer units. Examples of such monomer units include, for example, 3-hydroxybutyrate, glycolic acid, 3-hydroxypropionate, 3-hydroxyvalerate, 3-hydroxyhexanoate, 3-hydroxyheptanoate, 3-hydroxyoctanoate, 3-hydroxynonaoate, 3-hydroxydecanoate, 3-hydroxydodecanoate, 3-hydroxydodecenoate, 3-hydroxytetradecanoate, 3-hydroxyhexadecanoate, 3-hydroxyoctadecanoate, 4-hydroxybutyrate, 4-hydroxyvalerate, 5-hydroxyvalerate, and 6-hydroxyhexanoate.

In some embodiments, the PHA has at least one monomer unit with the chemical formula —$OCR_1R_2(CR_3R_4)_nCO$—. n is zero or an integer (e.g., one, two, three, four, five, six, seven, eight, nine, 10, 11, 12, 13, 14, 15, etc.). Each of $R_1$, $R_2$, $R_3$ and $R_4$ is a hydrogen atom, a saturated hydrocarbon radical or an unsaturated hydrocarbon radical. $R_1$ is the same as or different from each of $R_2$, $R_3$ and $R_4$. $R_2$ is the same as or different from each of $R_1$, $R_3$ and $R_4$. $R_3$ is the same as or different from each of $R_2$, $R_1$ and $R_4$, and $R_4$ is the same as or different from each of $R_2$, $R_3$ and $R_1$.

In some embodiments, the PHA is a homopolymer. Examples of such homopolymers include poly-4-hydroxybutyrate, poly-4-hydroxyvalerate, poly-3-hydroxypropionate, poly-3-hydroxybutyrate, poly-3-hydroxyhexanoate, poly-3-hydroxyheptanoate, poly-3-hydroxyoctanoate, poly-3-hydroxydecanoate and poly-3-hydroxydodecanoate. In some embodiments, the PHA is a copolymer that contains two or more different monomer units. Examples of such copolymers include poly-3-hydroxybutyrate-co-3-hydroxypropionate, poly-3-hydroxybutyrate-co-3-hydroxyvalerate, poly-3-hydroxybutyrate-co-3-hydroxyhexanoate, poly-3-hydroxybutyrate-co-4-hydroxybutyrate, poly-3-hydroxybutyrate-co-4-hydroxyvalerate, poly-3-hydroxybutyrate-co-6-hydroxyhexanoate, poly 3-hydroxybutyrate-co-3-hydroxyheptanoate, poly-3-hydroxybutyrate-co-3-hydroxyoctanoate, poly-3-hydroxybutyrate-co-3-hydroxydecanoate, poly-3-hydroxybutyrate-co-3-hydroxydodecanotate, poly-3-hydroxybutyrate-co-3-hydroxyoctanoate-co-3-hydroxydecanoate, poly-3-hydroxydecanoate-co-3-hydroxyoctanoate, and poly-3-hydroxybutyrate-co-3-hydroxyoctadecanoate.

The PHA can have a polystyrene equivalent weight average molecular weight of at least about 500 Daltons (e.g., at least about 10,000 Daltons, at least about 50,000 Daltons) and/or less than about 2,000,000 Daltons (e.g., less than about 1,000,000 Daltons, less than about 800,000 Daltons). As used herein, weight average molecular weight is determined by gel permeation chromatography, using e.g., chloroform as both the eluent and diluent for the PHA samples. Calibration curves for determining molecular weights can be generated using polystyrene molecular weight standards.

In certain embodiments in which the PHA is a poly-3-hydroxybutyrate copolymer (e.g., poly-3-hydroxybutyrate-co-3-hydroxypropionate, poly-3-hydroxybutyrate-co-3-hydroxyvalerate, poly-3-hydroxybutyrate-co-3-hydroxyhexanoate and/or poly-3-hydroxybutyrate-co-4-hydroxybutyrate, poly-3-hydroxybutyrate-co-3-hydroxyoctanoate-co-3-hydroxydecanote-co-3-hydroxydodecanote), the majority of the monomer units are 3-hydroxybutyrate (e.g., at least about 50% of the monomer units are 3-hydroxybutyrate, at least about 60% of the monomer units are 3-hydroxybutyrate).

In bacteria, each PHA monomer is produced by a specific pathway. In the case of the short pendant group PHAs, three enzymes are involved, a beta-ketothiolase (FIG. 2, Reaction 8), an acetoacetyl-CoA reductase (FIG. 2, Reaction 9), and a PHA synthase (FIG. 2, Reaction 10). Short chain length PHA synthases typically allow polymerization of C3-C5 hydroxy acid monomers including both 4-hydroxy and 5-hydroxy acid units. This biosynthetic pathway is found in a number of bacteria such as *Ralstonia eutropha, Alcaligenes latus, Zoo-*

*gloea ramigera.* Etc. (Madison, L. L. & Huisman, G. W. Microbiology and Molecular Biology Reviews 1999, 63, 21-53). Activities to promote short chain length PHA synthesis can be introduced into a host plant via a single transformation event. If necessary, genes encoding the enzymes can be fused to a DNA sequence encoding a peptide targeting signal that targets the mature protein after splicing to a particular compartment of the cell.

Figure 3:
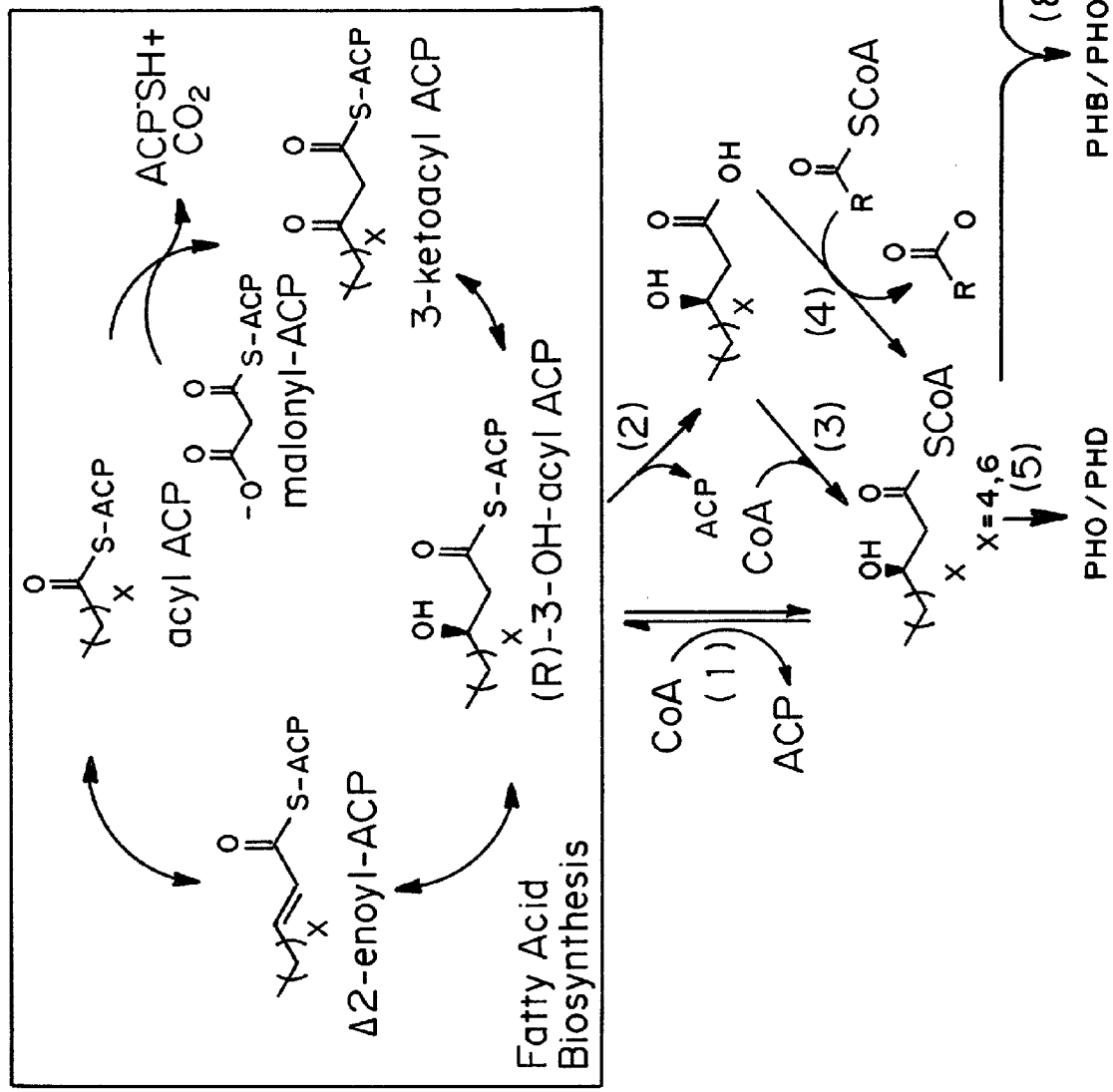
FIG. 3 is a schematic of a pathway for medium chain length PHA production from fatty acid biosynthesis. Activities to promote PHA synthesis from fatty acid biosynthesis can be selected from the following: 3-hydroxyacyl-acyl carrier protein-coenzyme A transferases (Reaction 1), thioesterases (Reaction 2), acyl CoA synthetases (Reaction 3), CoA transferases (Reaction 4), medium chain length synthases (Reaction 5), beta-ketothiolases (Reaction 6), NADH or NADPH dependent reductases (Reaction 7), and PHA synthases that incorporate both short and medium chain length substrates (Reaction 8). Selected activities can be produced in the host plant by transformation of the appropriate genetic construct(s).

Medium chain length pendant group PHAs are produced by many different *Pseudomonas* bacteria. The hydroxyacyl-coenzyme A monomeric units can originate from fatty acid beta-oxidation (FIG. 2) and fatty acid biosynthetic pathways (FIG. 3). The monomer units are then converted to polymer by PHA synthases which have substrate specificity's favoring the larger C6-C14 monomeric units (FIG. 2, Reaction 7; FIG. 3, Reaction 5; Madison, L. L. & Huisman, G. W. Microbiology and Molecular Biology Reviews 1999, 63, 21-53). Activities to promote medium chain length PHA synthesis from fatty acid beta-oxidation pathways can be introduced into a host plant via a single transformation event are selected from the enzymes described in FIG. 2, Reactions 1-7. If necessary, genes encoding the enzymes can be fused to a DNA sequence encoding a peptide targeting signal that targets the proteins to a particular compartment of the cell.

An enzymatic link between PHA synthesis and fatty acid biosynthesis has been reported in both *Pseudomonas putida* and *Pseudomonas aeruginosa* (FIG. 3, Reaction 1). The genetic locus encoding the enzyme believed to be responsible for diversion of carbon from fatty acid biosynthesis was named phaG (Rehm, et al. *J. Biol. Chem.* 1998, 273, 24044-24051; WO 98/06854; U.S. Pat. No. 5,750,848; Hoffmann, N., Steinbuchel, A., Rehm, B. H. A. FEMS Microbiology Letters, 2000, 184, 253-259). U.S. Pat. No. 6,586,658 describes additional genes useful for producing PHAs from fatty acid biosynthetic pathways. Activities to promote medium chain length PHA synthesis from fatty acid biosynthesis pathways can be introduced into a host plant via a single transformation event with a construct wherein the enzymes are selected from those described in FIG. 3, Reactions 1-3. If necessary, genes encoding the enzymes can be fused to a DNA sequence encoding a peptide targeting signal that targets the mature protein to a particular compartment of the cell, for example, the plastid.

Co-polymers comprised of both short and medium chain length pendant groups can also be produced in bacteria possessing a PHA synthase with a broad substrate specificity (FIG. 2, Reaction 11; FIG. 3, Reaction 5). For example, *Pseudomonas* sp. A33 (Appl. Microbiol. Biotechnol. 1995, 42, 901-909), *Pseudomonas* sp. 61-3 (Kato, et al. *Appl. Microbiol. Biotechnol.* 1996, 45, 363-370), and *Thiocapsa pfennigii* (U.S. Pat. No. 6,011,144) all possess PHA synthases that have been reported to produce co-polymers of short and medium chain length monomer units. Activities to promote formation of co-polymers of both short and medium chain length pendant groups can be introduced into a host plant via a single transformation event and can encode polypeptides catalysing reactions 1-11 for fatty acid degradation routes (FIG. 2) and reactions 1-8 for fatty acid biosynthesis routes in FIG. 3. If necessary, genes encoding these polypeptides can be fused to a DNA sequence encoding a peptide targeting signal that targets the mature protein after to a particular compartment of the cell for example the plastid.

Additional pathways for incorporation of 3-hydroxyvalerate are described by PCT WO 98/00557 by Gruys et. al. Pathways for incorporation of 4-hydroxybutyrate are elaborated in PCT WO 98/36078 by Dennis and Valentin and PCT WO 99/14313 by Huisman et. al.

Prior to producing PHAs from plants on an industrial scale, polymer production in crops of agronomic value should be optimized. Preliminary studies in some crops of agronomic value have been performed (for review see Bohmert et al., 2004 Metabolic Engineering: Plastids as Bioreactors. In *Molecular Biology and Biotechnology of Plant Organelles*, H. Daniell and C. D. Chase, Editors. Kluwer Academic Publishers: Netherlands. p. 559-585) including PHB production in maize (Poirier & Gruys, 2002, Production of polyhydroxyalkanoates in transgenic plants. In *Biopolymers*, A. Steinbüchel, Editor. Wiley-VHC Verlag GmbH: Weinheim. p. 401-435) as well as PHB production in transgenic canola and soybean seeds (Gruys et al., PCT WO 98/00557). In these studies, the levels of polymer observed were too low for economical production of the polymer. Optimization of PHA production in crops of agronomic value utilizes the screening of multiple enzymes, targeting signals, and sites of production until a high yielding route to the polymer with the desired composition is obtained. This is a task which can be simplified if multiple genes are inserted in a single transformation event. The creation of multi-gene expression constructs is useful for reducing the complexity of the traditional breeding methodology required to make the transgenic plant agronomically useful.

The present invention will be further understood by reference to the following non-limiting examples.

EXAMPLES

Example 1

Construction of Plasmids

All DNA manipulations, including PCR, DNA sequencing, transformation, and plasmid purification, were performed using standard procedures, as described, for example, by Sambrook et. al., Molecular Cloning: A Laboratory Manual (Cold Spring Harbor Laboratory Press, New York (1989)).

pUC18-C4PPDK-AAA-RBS contains the 35S-C4PPDK promoter (Chiu et al. *Curr. Biol.* 6: 325 (1996)), DNA encoding the signal peptide of the small subunit of rubisco from pea and the first 24 aa of the mature protein (Coruzzi et al. *J Biol. Chem.* 258(3):1399-1402 (1983)), DNA encoding a three aa linker that contains a Xba I restriction site allowing fusion of the desired transgene, and the 3' terminator of the nopaline synthase gene (Bevan et al., *Nucleic Acids Res.* 11(2):369-385 (1983)). This plasmid was constructed using the following multi-step procedure. Oligonucleotides BamXbaNot-A and BamXbaNot-B were annealed and ligated into plasmid pUC18-35S-C4PPDKsGFPnos (Chiu et al. *Curr. Biol.* 6: 325 (1996)) that had been previously digested with BamH I and Not I. The resulting plasmid was named pUC18-35S-C4PPDK-BXNP-nos. The rubisco chloroplast targeting signal and the first 24 aa of the mature protein were amplified from genomic DNA obtained from expanded young green leaves of *Pisum sativum* Progress #9 using primers PEATSC and PEATSR. The resulting 0.34 kbp fragment was cloned into the BamH I and Xba I sites of pUC18-35S-C4PPDK-BXNP-nos forming plasmid pUC18-35S-C4PPDK-P.t.s.nos. To remove the intron from the pea targeting signal, plasmid pUC18-35S-C4PPDK-P.t.s.nos was digested with Sph I and Mfe I. Linkers P.t.s.nointron A and P.t.s.nointron B were annealed and ligated into the Sph I and Mfe I sites of pUC18-35S-C4PPDK-P.t.s.nos to create pUC18-C4PPDK-rbcs-nos. The start site of the signal sequence from plasmid pUC18-C4PPDK-rbcs-nos was optimized for plant expression by changing the existing TCCATGG sequence to AAAATGG using the QuikChange® Site-Directed Mutagenesis Kit (Stratagene, La Jolla, Calif.) to form plasmid pUC-C4PPDK-AAA-RBS-nos.

pCAM(RBCS-link) is derived from the pCAMBIA2300 binary vector (Center for Application of Molecular Biology to International Agriculture, Canberra, Australia) and contains the promoter, signal sequence, and terminator fragment previously described for plasmid pUC18-C4PPDK-AAA-RBS. Plasmid pCAM(RBCS-link) was constructed with the following multi-step procedure. Double stranded synthetic linkers 1 and 2 were made by annealing oligonucleotides 1A and 1B, and oligonucleotides 2A and 2B, respectively. The promoter, signal sequence, and terminator were excised from plasmid pUC-C4PPDK-AAA-RBS-nos using unique EcoR I and Xho I sites. The resulting 1.1 kbp fragment was annealed to linkers 1 and 2 to create a promoter, signal sequence, and terminator DNA fragment flanked on the 5' end by Hind III, BstB I, Pac I, Xho I restriction sites and on the 3' end by EcoR I, Pac I, Asc I, Avr II, and Sac I sites. This fragment was cloned into the Sac I and Hind III sites of the plant transformation vector pCAMBIA2300 to create pCAM(RBCS-link).

pCAM(A) was created by amplifying the phaA gene from pAeT10 (Peoples and Sinskey, *J Biol Chem.* 264(26):15293-7. (1989)) using primers AB-F and A-R. The resulting fragment was cloned into the Xba I and Pst I sites of pCAM (RBCS-link) to create a translational fusion of the pea targeting signal with the phaA gene.

pCAM(B) was created by amplifying the phaB gene from pAeT10 (Peoples and Sinskey, *J. Biol. Chem.* 264(26):15293-7 (1989)) using primers B-F and AB-R and cloning the DNA fragment into pCAM(RBCS-link) using the procedure previously described for pCAM(A).

pCAM(C) was created by amplifying the synthase gene from pCMYS106, a pUC19 (Yanisch-Perron et al., *Gene* 33: 103-119 (1985)) based plasmid containing a hybrid *Pseudomonas oleovorans/Zoogloea ramigera* synthase (U.S. Pat. No. 6,316,262), using primers C—F and C—R. The PCR product was digested with Xba I and Nsi I. The resulting fragment was cloned into the compatible cohesive ends of the Xba I and Pst I sites of pCAM(RBCS-link) to create pCAM (C).

pCAM(C+A+B) was constructed using a two step process. pCAM(A+B) was created by removing the phaA cassette from pCAM(A) using the 5' BstB I and 3' Avr II sites, blunting the BstB I site, and cloning the resulting insert into the Avr II and blunted Asc I sites of pCAM(B). pCAM(C+A+B) was created by removing the phaA and phaB cassettes from pCAM(A+B) using the 5' BstB I and 3' Avr II sites, blunting the BstB I site, and cloning this insert into the Avr II and blunted Asc I sites of pCAM(C). This constitutive PHB expression vector is designated CAB.

pNEB(greA)—The constitutive thiolase expression cassette including the 35S-C4PPDK promoter, the plastid targeting signal, the thiolase gene and the polyadenylation signal were removed from pCAM(A) (Kourtz et al., *Plant Biotechnol.* 3: 435-447 (2005)) using an Asc I and Pme I digest. The resulting fragment was cloned into the Asc I and Pme I sites of pNEB193 (New England Biolabs, Beverly, Mass.) to create pNEB(A). The glucocorticoid inducible minimal promoter 6gre-6035SCaMV was removed from pBL221.9GRE6 (Martinez et al. *Plant J.* 19: 97-106 (1999)) using a Hind III and a blunted Nco I digest. The resulting fragment was cloned into the Sma I and Hind III sites of pNEB193 to create pNEB(greMP). The constitutive 35SC4PPDK promoter of pNEB(A) was swapped for the inducible promoter of pNEB (greMP) using the Seamless Cloning™ technique (Stratagene, La Jolla, Calif.). The inducible minimal promoter was amplified from pNEB(greMP) in such a way as to contain unique 3' and 5' Eam1104 I restriction sites using primers LK50 (ATTTC CTCTTCAGAGCAGCTATGACCATGATTACGCCAAGC TTCGAC TG)(SEQ ID NO:1), LK51 (TCGGT CTCTTCATTTCGATACCCGATCCCCCGTGTTCTCTCC AAATG) (SEQ ID NO:2).

Primers LK52 and (TTGCT CTCTTCAAAAATGGCTTCTATGATATCCTCTTCCGCT GTGACA ACAGTCAGCCGTGCCTCTAGG) (SEQ ID NO:3) LK53 (TGGAG CTCTTCACTCGAGTTAATTAATTCGAAAAGCTTGGC ACTGGC CG) (SEQ ID NO:4) were used to PCR almost the entire pNEB(A) plasmid including the vector backbone, the plastid targeting signal, the thiolase gene and the polyadenylation signal, but not the 35S-C4PPDK constitutive promoter, in such a way that the resulting fragment was flanked by unique 3' and 5' Eam1104 I restriction sites. PCR reactions were performed essentially as recommended by the manufacturer. The resulting PCR products were digested with Eam1104 I and ligated to produce pNEB(greA). Correct products were identified by screening for the BamH I site located in the inducible minimal promoter, but absent in the constitutive promoter.

pCAM(greA), pCAM(greB) and pCAM(greC)-pNEB (greA) were cut with BstB I and Xba I to yield the GRE-60 MP-TS fragment that contains the glucocorticoid response elements (GRE), the minimal 35S promoter from the cauliflower mosaic virus (−60 MP) and the RBCS targeting signal (TS). The constitutive promoter and targeting signal of pCAM(A), pCAM(B) or pCAM(C) (Kourtz et al., *Plant Biotechnol.* 3: 435-447 (2005) were removed via a BstB I and Xba I digest. The resulting vectors were ligated to the GRE-60 MP-TS fragment to produce pCAM(greA), pCAM(greB), and pCAM(greC).

pCAM(CgreAB)—The inducible thiolase cassette, greA, containing the minimal inducible promoter, the signal sequence and the thiolase phbA gene was removed from pCAM(greA) with a BstB I and an Avr II digest. The BstB I site was blunted and the resulting sticky-blunt fragment was cloned into the Avr II and blunted Asc I sites of pCAM(C) to produce pCAM(CgreA). Using the same procedure, the constitutive reductase cassette was added to pCAM(CgreA) to produce pCAM(CgreAB), pCAM(C) and pCAM(B).

pUC18-C4PPDK-AAA-RBS contains the 35S-C4PPDK promoter (Chiu et al. *Curr. Biol.* 6: 325 (1996)), DNA encoding the signal peptide of the small subunit of rubisco from pea and the first 24 aa of the mature protein (Coruzzi et al. *J Biol Chem.* 258(3):1399-1402 (1983)), DNA encoding a three aa linker that contains a Xba I restriction site allowing fusion of the desired transgene, and the 3' terminator of the nopaline synthase gene (Bevan et al., *Nucleic Acids Res.* 11(2):369-85. (1983)). This plasmid was constructed using the following multi-step procedure. Oligonucleotides BamXbaNot-A and BamXbaNot-B were annealed and ligated into plasmid pUC18-35S-C4PPDKsGFPnos (Chiu et al. *Curr. Biol.* 6: 325 (1996)) that had been previously digested with BamH I and Not I. The resulting plasmid was named pUC18-35S-C4PPDK-BXNP-nos. The rubisco chloroplast targeting signal and the first 24 aa of the mature protein were amplified from genomic DNA obtained from expanded young green leaves of *Pisum sativum* Progress #9 using primers PEATSC and PEATSR. The resulting 0.34 kbp fragment was cloned into the BamH I and Xba I sites of pUC18-35S-C4PPDK- BXNP-nos forming plasmid pUC18-35S-C4PPDK-P.t.s.nos. To remove the intron from the pea targeting signal, plasmid pUC18-35S-C4PPDK-P.t.s.nos was digested with Sph I and Mfe I. Linkers P.t.s.nointron A and P.t.s.nointron B were annealed and ligated into the Sph I and Mfe I sites of pUC18-35S-C4PPDK-P.t.s.nos to create pUC18-C4PPDK-rbcs-nos. The start site of the signal sequence from plasmid pUC18-C4PPDK-rbcs-nos was optimized for plant expression by changing the existing TCCATGG sequence to AAAATGG using the QuikChange® Site-Directed Mutagenesis Kit (Stratagene, La Jolla, Calif.) to form plasmid pUC-C4PPDK-AAA-RBS-nos.

pCAM(RBCS-link) is derived from the pCAMBIA2300 binary vector (Center for Application of Molecular Biology to International Agriculture, Canberra, Australia) and contains the promoter, signal sequence, and terminator fragment previously described for plasmid pUC18-C4PPDK-AAA-RBS. Plasmid pCAM(RBCS-link) was constructed with the following multi-step procedure. Double stranded synthetic linkers 1 and 2 were made by annealing oligonucleotides 1A and 1B, and oligonucleotides 2A and 2B, respectively. The promoter, signal sequence, and terminator were excised from plasmid pUC-C4PPDK-AAA-RBS-nos using unique EcoR I and Xho I sites. The resulting 1.1 kbp fragment was annealed to linkers 1 and 2 to create a promoter, signal sequence, and terminator DNA fragment flanked on the 5' end by Hind III, BstB I, Pac I, Xho I restriction sites and on the 3' end by EcoR I, Pac I, Asc I, Avr II, and Sac I sites. This fragment was cloned into the Sac I and Hind III sites of the plant transformation vector pCAMBIA2300 to create pCAM(RBCS-link).

pCAM(AB) was created by amplifying the phaA-phaB fusion gene from pTRC(AB), a plasmid containing the phaA-phaBfusion (WO00/06747; Kourtz et al. *Plant Biotechnol.* 3: 435-447 (2005)) using primers AB-F and AB-R. The resulting fragment was cloned into the Xba I and Pst I sites of pCAM(RBCS-link) to create a translational fusion of the pea targeting signal with the phaA-phaB gene.

pCAM(A) was created by amplifying the phaA gene from pAeT10 (Peoples and Sinskey, *J Biol Chem.* 264(26):15293-7. (1989)) using primers AB-F and A-R. The resulting fragment was cloned into pCAM(RBCS-link) using the procedure previously described for pCAM(AB).

pCAM(B) was created by amplifying the phaB gene from pAeT10 (Peoples and Sinskey, *J Biol Chem.* 264(26):15293-7. (1989)) using primers B-F and AB-R and cloning the DNA fragment into pCAM(RBCS-link) using the procedure previously described for pCAM(AB).

pCAM(C) was created by amplifying the synthase gene from pCMYS106 (Kourtz et al., (2005) *Plant Biotechnol.* 3: 435-447) using primers C-F and C-R. The PCR product was digested with Xba I and Nsi I. The resulting fragment was cloned into the compatible cohesive ends of the Xba I and Pst I sites of pCAM(RBCS-link) to create pCAM(C).

pCAM(C+AB) was created by removing the phaA-phaB cassette from pCAM(AB) using the 5' BstB I and 3' Avr II sites. The BstB I site was blunted, and the resulting DNA fragment was cloned into the Avr II and blunted Asc I sites of pCAM(C).

pCAM(C+A+B) was constructed using a two step process. pCAM(A+B) was created by removing the phaA cassette from pCAM(A) using the 5' BstB I and 3' Avr II sites, blunting the BstB I site, and cloning the resulting insert into the Avr II and blunted Asc I sites of pCAM(B). pCAM(C+A+B) was created by removing the phaA and phaB cassettes from pCAM(A+B) using the 5' BstB I and 3' Avr II sites, blunting the BstB I site, and cloning this insert into the Avr II and blunted Asc I sites of pCAM(C).

pCAM(greCgreAgreB). The inducible thiolase cassette, greA, containing the minimal inducible promoter, the signal sequence and the thiolase phbA gene was removed from pCAM(greA) with a BstB I and an Avr II digest. The BstB I site was blunted and the resulting sticky-blunt fragment was cloned into the Avr II and blunted Asc I sites of pCAM(greC) to produce pCAM(greCgreA). Using the same procedure, the inducible reductase cassette was added to pCAM(greCgreA) to produce pCAM(greCgreAgreB). pNEB(e35Sgrvhnos). The chimeric ecdysone receptor containing the glucocorticoid DNA binding domains, the VP16 transactivation domain and the *Heliothis virescens* ecdysone receptor was removed from pMF6GRVP16HEcR, an intron containing pMF6 (Goff et al., (1990) *EMBO J.* 9: 2517-2522). derivative of the pGRVHEcR plasmid described by Martinez and colleagues (Martinez, et al. (1999b) *Plant J* 19: 97-106.), using a BamH I digest. The resulting fragment was cloned into the BamH I site of pNEB193 to produce pNEB(grvh). The double enhanced 35S promoter from the cauliflower mosaic virus (e35SCaMV) promoter was removed from pCAM2300 (CAMBIA, Canberra, Australia) using a Nco I and a blunted BstX I digest. The resulting fragment was cloned into the EcoR V and Nco I sites of pNEB(grvh) to create pNEB (e35Sgrvh). The 3' Asc I site of this vector was removed by digesting with Asc I, blunting with DNA Polymerase I Klenow fragment followed by re-ligating the vector with T4 DNA ligase to create pNEB(e35SgrvhΔAscI). The 3'UTR of the nopaline synthase gene was removed from pMF6GRVP16HEcR via PCR using the oligonucleotides nosF (CCTTAATTAACTCGAGGAATTCATCGAT-TCCGCGGGTACCGAG) (SEQ ID NO:5) and nosR (GCTCTAGACCTAGGGGCGCGCCA-GATCTAGTAACATAGATGACACC GCGCGCGATAATT-TATCCTAGTTTGCG) (SEQ ID NO:6). These primers introduce a 5' Pac I site and 3' Asc I, Avr II and Xba I sites to the nos fragment. The resulting PCR product was cloned into the Pac I and Xba I sites of pNEB(e35SgrvhΔAscI) to create pNEB (e35Sgrvhnos). pCAM(CgreABgrvh) and pCAM (greCgreAgreBgrvh). The effector cassette containing the chimeric ecdysone receptor, the constitutive promoter and polyadenylation sequence was removed from pNEB(35S-grvh-nos) via an Avr II and blunted Spe I digest. The resulting fragment was cloned into the Avr II and blunted Asc I sites of pCAM(CgreAB) and pCAM(greCgreAgreB) to produce pCAM(CgreABgrvh) and pCAM(greCgreAgreBgrvh).

Example 2

Plant Transformation and Induction

The genes required for the complete PHB production pathway, a ketothiolase (thiolase), an NADPH-acetoacetyl-CoA reductase (reductase) and a PHA synthase (synthase), were individually placed under the control of the minimal 35S ecdysone-inducible promoter, fused to a plastid targeting signal, and cloned into a pCAMBIA (Centre for Application of Molecular Biology to International Agriculture, Canberra, Australia) based multigene plasmid containing the chimeric ecdysone receptor (A. Martinez, C. Sparks, C. A. Hart, J. Thompson, I. Jepson, *Plant J.* 19: 97 (1999)). This three-gene inducible construct is designated 3I. The single-gene inducible construct designated 1I contained the thiolase gene under the control of the inducible promoter, but unlike the 3I construct, it expressed the reductase and synthase genes under the control of the constitutive 35S-C4PPDK promoter (W. Chiu et al. *Curr. Biol.* 6: 325 (1996)).

Transformation of *Arabidopsis* was performed as described in Clough and Bent (S. J. Clough, A. F. Bent, *Plant J.* 16: 735 (1998)) as follows: Electrocompetent cells of *Agrobacterium* strain GV3101/pMP90 (Koncz and Schell, *Mol. Gen. Genetics* 204: 383-396 (1986)) were transformed with plasmid DNA and single colonies were isolated on LB plates containing gentamycin and kanamycin. *Arabidopsis thaliana* Columbia Col-0 (Lehle Seeds, Round Rock, Tex.) was grown in soil at 20° C., 70% humidity, and a 16 hour light, 8 hour dark cycle. Plants were transformed using an *Agrobacterium*-mediated floral dip procedure described by Clough and Bent *Plant J.* 16: 735 (1998)). Seeds from mature siliques were harvested, sterilized, and spread onto selection plates containing ½× Murashige Minimal Organics Medium (Life Technologies, Rockville, Md.), 0.7% agar, 1× Gamborg's B5 vitamins (Sigma, St. Louis, MO), and kanamycin (50 μg/mL). Plates were incubated for two days at 4° C. and transferred to 20° C., 70% humidity, and a 16 hour light, 8 hour dark cycle. After seven days, green kanamycin resistant seedlings were transferred to soil and incubated at the same growth conditions until plants were ready for analysis.

*Arabidopsis* plants were grown until they reached full size under routine growth conditions. Upon reaching maturity at approximately 30 days old, the plants were subjected to treatment with inducing agent via root drenching or foliar application. Inducing agents employed include tebufenozide, Mimic® and Intrepid®. The commercial pesticides Mimic® and Intrepid® (available from UAP Timberland (Monticello, Ark.) and Polina Chemical Compounds (Hatfield, Mass.)) were employed as inducing agents since their respective active ingredients, tebufenozide and methoxyfenozide, are non-steroidal ecdysone analogs. Root drenching involved diluting the inducing agent to the desired concentration in ¼× Hoaglands fertilizer solution (Sigma, St. Louis, Mo.) and applying ten mL of the resulting solution directly to the soil of each *Arabidopsis* plant. During foliar application, plants were first watered with ¼× Hoaglands fertilizer solution. Diluted inducing agent was then sprayed directly onto the leaves of the *Arabidopsis* plants until the leaf surface was saturated and dripping. Root drenching and foliar applications of inducing agent were repeated twice a week for three weeks until the plants set seed.

Example 3

Plant PHB Analysis and Extraction

Fluorescence microscopy with Nile Blue staining was performed as previously described (Poirier et al. *Science* 256: 520-523 (1992)) with some modifications. Leaf tissue was sliced as thin as possible with a razor blade and fixed in 3% paraformaldehyde (Electron Microscopy Sciences, Ft. Washington, Pa.) in 0.1 M $K_2PO_4$, pH 8, for three hours. Fixed samples were washed with water and stained with a previously filtered 1% Nile Blue (Sigma, St. Louis, Mo.) solution for five minutes at room temperature. Samples were washed with water and destained with 8% acetic acid. Samples were washed an additional two times with water. Samples were viewed by fluorescence microscopy on a Zeiss Axiolab light microscope equipped with a Zeiss HBO 100 fluorescence attachment and a 20×Ph-1 lens using the following filter set: exciter, HQ545/30; beam splitter, Q570lp; emitter D590/20 (Chroma Technology, Brattleboro, Vt.). Images were recorded with a Zeiss MC 80 DX Microscope Camera using Kodak Elite Chrome 100 film.

Plant polymer analysis was performed essentially as described in Kourtz et al. (Kourtz et al., *Plant Biotechnol.* 3: 435-447 (2005)) with the following modifications. The initial step involving pre-washing of the plant material was omitted prior to the dried plant material being derivatized by butanolysis and extraction of the impurities with water. The resulting organic phase was analyzed by gas chromatography/mass spectroscopy using an Agilent 5973 GC/MS in selected ion monitoring mode equipped with a DB-225MS column and guard. The selected ions of the butyl-3-hydroxybutyrate ester were 87, 89, and 43.1 amu.

For PHB extraction, inducible $T_4$ 3I *Arabidopsis* plants were treated to foliar applications of 0.5 mM Intrepid®. Tissue was harvested and dried prior to PHB extraction using standard non-aqueous protocols.

Example 4

PHB Yields in Treated and Untreated $T_1$ 1I and 3I *Arabidopsis* Plants

A total of Eighty-six mature 30 day old first generation $T_1$ transgenic plants transformed respectively with either the 1I construct and 108 mature 30 day old $T_1$ transgenic plants transformed with the 3I construct were treated with foliar applications of 0.5 mM Intrepid® or left untreated.

Plants expressing the three-gene inducible construct 3I accumulated up to 10% dwt PHB upon treatment with inducing agent. Interestingly, the highest PHB-producing treated 3I plants developed leaf chlorosis during the course of induction, but this phenotype was not observed in untreated plants. Untreated 3I plants failed to accumulate more than 0.37% dwt PHB, and on average they produced a factor of six less % dwt PHB than treated plants expressing the same construct (Table I).

By contrast, plants transformed with the 1I construct failed to accumulate high levels of PHB, producing less than 0.039% dwt PHB in the presence or absence of inducing agent (Table I). This result was unexpected because the inducible thiolase cassette of the 1I construct participated in the production of high levels of PHB in 3I plants. In addition, the constitutive reductase and synthase cassettes of the 1I construct, in the presence of a constitutive thiolase, have previously been shown to catalyze the production of 11.5% dwt PHB in constitutive *Arabidopsis* plants. Further analysis of the 1I construct by screening an additional 235 $T_1$ 1I plants identified plants capable of producing 2.5% and 2.6% dwt PHB respectively, in the presence and absence of foliar applications of the inducing agent tebufenozide. The ability of this construct to promote PHB production in a non-inducible fashion was confirmed through analysis of 72 $T_2$ offspring of the best $T_1$ 1I plant. Treated and untreated $T_2$ 1I plants accumulated on average 4.2±2.5% and 4.7±1.4% dwt PHB, respectively in the presence and absence of inducing agent. Collectively, these results demonstrate that optimal inducible PHB production does not occur unless all of the genes of the PHB production pathway are induced simultaneously.

TABLE I

PHB yields in treated and untreated $T_1$ 1I and 3I *Arabidopsis* plants. Treated plants were subjected to foliar applications of 0.5 mM Intrepid ®. The average and standard error are shown.

| Transgenic Plant Line | Sample size (n) | Treatment | Average Total PHB content (% dwt) | Average PHB of Best Three Plants (% dwt) | Highest yield of PHB (% dwt) |
|---|---|---|---|---|---|
| 1I | 27 | untreated | 0.009 ± 0.005 | 0.021 ± 0.007 | 0.025 |
| 1I | 59 | treated | 0.019 ± 0.010 | 0.038 ± 0.001 | 0.039 |

TABLE I-continued

PHB yields in treated and untreated $T_1$ 1I and 3I *Arabidopsis* plants. Treated plants were subjected to foliar applications of 0.5 mM Intrepid ®. The average and standard error are shown.

| Transgenic Plant Line | Sample size (n) | Treatment | Average Total PHB content (% dwt) | Average PHB of Best Three Plants (% dwt) | Highest yield of PHB (% dwt) |
|---|---|---|---|---|---|
| 3I | 27 | untreated | 0.110 ± 0.084 | 0.288 ± 0.073 | 0.367 |
| 3I | 81 | treated | 0.661 ± 1.487 | 7.708 ± 2.072 | 10.055 |

Example 5

Increases in PHB production in Young Tissue of $T_2$ 3I Plants Root Drenched with 0.1 mM Mimic® or Left Untreated 3I plants were treated with 0.1 mM Mimic® via root drenching, a technique believed to promote ecdysteroid assimilation through the roots (E. Unger, et al., *Trans. Res.* 11, 455 (2002); Schena et al. *Proc. Natl. Acad. Sci. USA* 88, 10421 (1991)). The plants chosen for this study include the $T_2$ offspring of 3I plants 7, 11 and 12. These $T_1$ 3I plants had been shown to accumulate approximately 2% dwt PHB when sprayed with 1 mM Mimic®.

Analysis of $T_2$ plant phenotype revealed that untreated Line 7 plants remained green and healthy during the course of 18 days. By contrast, young leaves of root drenched Line 7 plants exhibited a stunted chlorotic phenotype that is characteristic of total leaf tissue of plants constitutively producing high levels of PHB (K. Bohmert et al., *Planta* 211, 841 (2000)). The phenotype exhibited by the treated inducible plants became readily apparent within 12 days of the initial application of Mimic® as green and healthy normal sized plants generated abnormally small yellow leaves. Similar results were obtained for Line 11 and Line 12 plants. This change in phenotype was not directly attributed to a negative reaction to Mimics and its components, as control plants transformed with the empty vector pCAM2300 remained green and healthy during root drenching with Mimics. In addition, constitutive PHB-producing control plants (CAB) remained chlorotic during treatment, produced young leaves in proportion with older leaf tissue and exhibited a phenotype similar to untreated CAB plants. Collectively, these data indicate that root drenching with Mimic® induces the expression of the genes required for PHB production, and that the resulting upsurge of PHB production triggers the production of abnormally small chlorotic leaves.

Quantitative GC/MS analysis was carried out on these plants as described above. Untreated Line 7, 11 and 12 plants contained less than 2% dwt PHB, but treated plants from the same lines accumulated in excess of 14% dwt PHB in young leaves (Table II). On average, the % dwt PHB observed in young tissue of $T_2$ 3I Line 7 plants was a factor of 12 greater than that detected in young tissue of untreated plants from the same line. Similar results were obtained with $T_2$ 3I Line 11 and 12 plants which showed an increase in PHB accumulation by a factor of 14 in young treated leaves relative to untreated young tissue. Examination of polymer content from individual Line 7 plants revealed that PHB content in young leaves increased by a factor of 37 after 21 days of root drenching (Table III). Increases in polymer production by factors of 179 and 316 were recorded in young treated tissue from Line 11 and 12, respectively (Table III). On average, young tissue from treated $T_2$ Line 7, 11 and 12 plants accumulated factors of 1.7, 2.8 and 2.0 more PHB respectively, than older tissue from the same plants (Table II). For example, the best $T_2$ Line 11 plant accumulated in excess of 14% dwt PHB in treated young leaves, but accumulated only 7.0% dwt PHB in older tissue (Table II).

TABLE II

PHB content of young and old leaves harvested from $T_2$ 3I plants that had been root drenched with 0.1 mM Mimic ® or left untreated. The PHB yield of the best plant is shown. The average and standard error for the PHB content of ten samples is shown.

| $T_2$ 3I Plant Line | Treatment | Tissue type | PHB Content (% dwt) best plant | average of n = 10 |
|---|---|---|---|---|
| 3I-7 | Mimic | young leaves | 10.00 | 3.68 ± 3.19 |
|  |  | old leaves | 4.60 | 2.14 ± 1.46 |
|  | untreated | young leaves | 0.59 | 0.32 ± 0.17 |
|  |  | old leaves | 1.58 | 0.64 ± 0.40 |
| 3I-11 | Mimic | young leaves | 14.32 | 6.98 ± 4.84 |
|  |  | old leaves | 6.96 | 2.45 ± 2.02 |
|  | untreated | young leaves | 0.92 | 0.49 ± 0.20 |
|  |  | old leaves | 0.44 | 0.45 ± 0.15 |
| 3I-12 | Mimic | young leaves | 12.65 | 9.02 ± 2.42 |
|  |  | old leaves | 4.54 | 4.40 ± 1.20 |
|  | untreated | young leaves | 1.97 | 0.66 ± 0.57 |
|  |  | old leaves | 1.42 | 0.77 ± 0.65 |

TABLE III

Increases in PHB production in young tissue of $T_2$ 3I plants root drenched with 0.1 mM Mimic ® or left untreated.

| $T_2$ 3I plant line | Treatment | PHB (% dwt) Day 0 | Day 21 | Fold Increase in % dwt PHB (Day 21/Day 0) |
|---|---|---|---|---|
| 7-135 | untreated | 0.87 | 0.22 | 0.25 |
| 7-138 | untreated | 0.07 | 0.27 | 3.86 |
| 7-146 | untreated | 0.23 | 0.11 | 0.46 |
| 7-150 | untreated | 0.06 | 0.25 | 4.17 |
| 7-31 | Mimic ® | 0.28 | 6.50 | 23.21 |
| 7-32 | Mimic ® | 0.27 | 10.00 | 37.04 |
| 7-35 | Mimic ® | 1.11 | 4.59 | 4.14 |
| 7-38 | Mimic ® | 0.74 | 4.33 | 5.81 |
| 7-39 | Mimic ® | 0.63 | 6.18 | 9.84 |
| 11-155 | untreated | 0.24 | 0.53 | 2.21 |
| 11-165 | untreated | 0.28 | 0.29 | 1.04 |
| 11-102 | Mimic ® | 0.06 | 5.43 | 90.50 |
| 11-105 | Mimic ® | 0.42 | 8.42 | 20.05 |
| 11-106 | Mimic ® | 0.08 | 14.32 | 179.00 |
| 11-111 | Mimic ® | 0.12 | 8.96 | 74.67 |
| 11-119 | Mimic ® | 0.05 | 5.90 | 118.00 |
| 11-121 | Mimic ® | 0.12 | 5.30 | 44.17 |
| 12-113 | Mimic ® | 0.04 | 10.09 | 252.25 |
| 12-119 | Mimic ® | 0.04 | 12.65 | 316.25 |

Example 6

PHB yields in $T_3$ 3I Plants Subjected to Root Drenching or Foliar Applications with Increasing Concentrations of Mimic® and Intrepid®

Figure 7A:
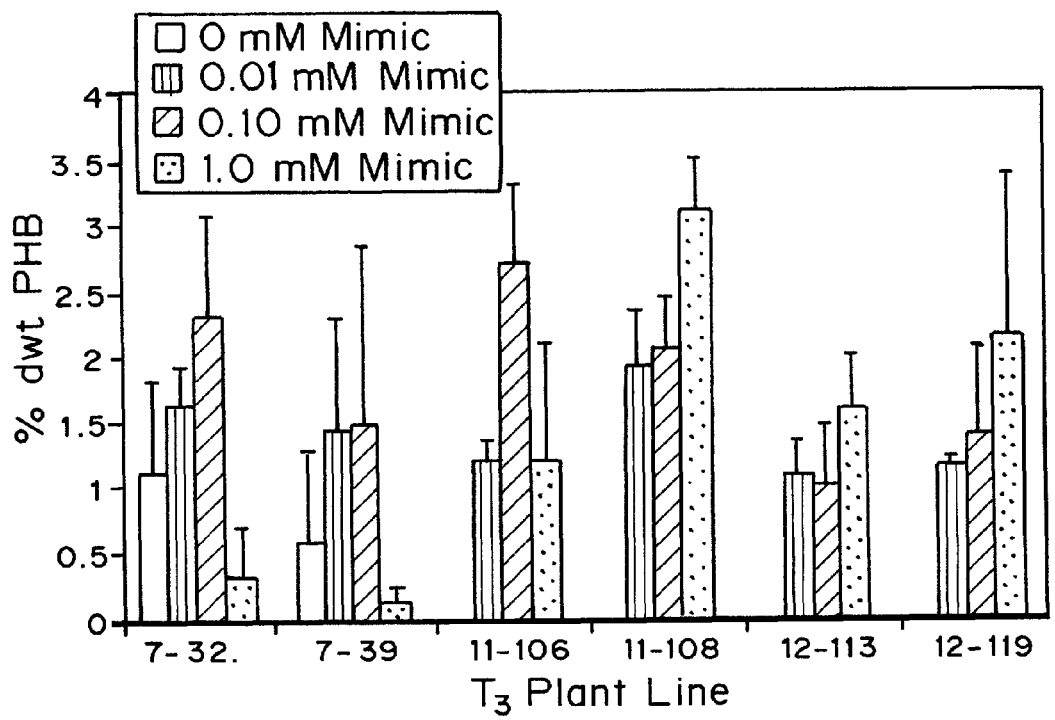
FIG. 7 shows PHB yields in third generation ($T_3$) 3I plants subjected to root drenching or foliar applications with increasing concentrations of Mimic® and Intrepid®. The average and standard error for four samples are shown. (A) PHB yields in $T_3$ 3I plants root drenched with various concentrations of Mimic®. (B) PHB yields in $T_3$ 3I plants root drenched with various concentrations of Intrepid®. (C) PHB yields in $T_3$ 3I plants treated with foliar applications of Intrepid®.

The progeny of the best $T_2$ 3I plants, Lines 7-32, 7-39, 11-106, 11-108, 12-113 and 12-119, were subjected to root drenching with increasing concentrations of Mimic®. Polymer production was induced by the addition of as little as 0.01 mM Mimic®, but PHB production was enhanced by treatment with either 0.1 mM (Lines 7-32, 7-39, 11-106) or 1.0 mM (Lines 11-108, 12-113, 12-119) Mimic® (FIG. 7A). For example, Lines 11-108 failed to produce PHB in the absence of inducing agent but accumulated on average 1.94±0.44 and 3.13±0.38% dwt PHB when treated with 0.01 mM and 1 mM Mimic®, respectively. The accumulation of low levels of polymer in Lines-7-32 and 7-39 in the absence of inducing agent suggests that these lines are leaky.

Figure 7B:
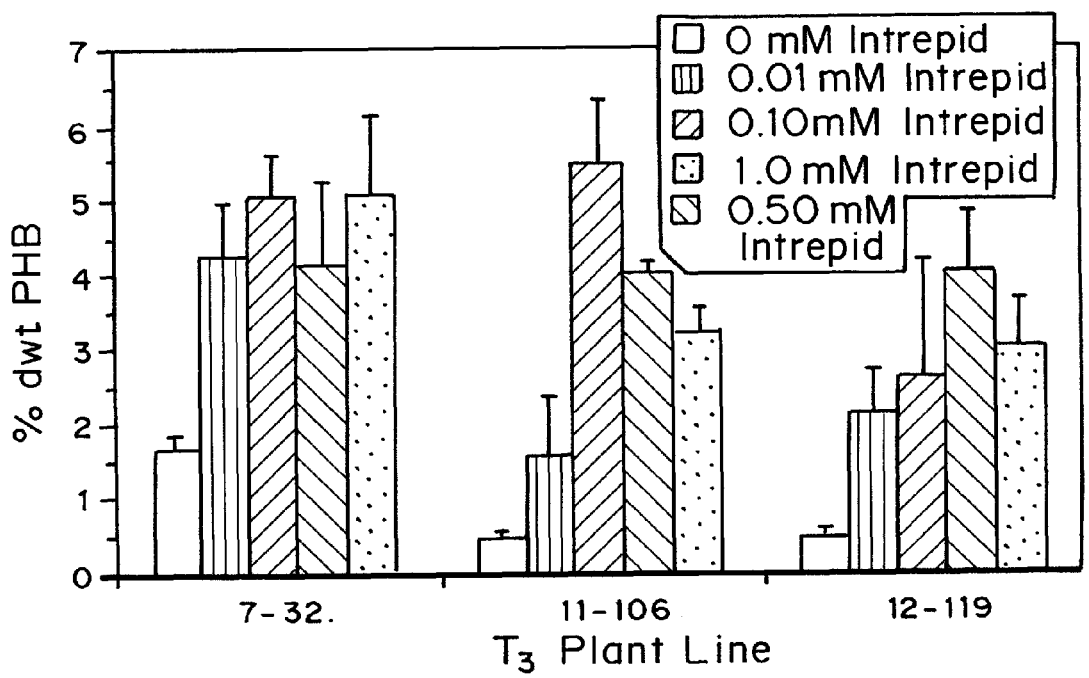

Similar results were obtained in root drench experiments with Intrepid®. Low levels of PHB were produced upon treatment with 0.01 mM Intrepid®, but enhanced PHB yields were obtained with 0.1 mM (Line 11-106), 0.5 mM (Line 12-119) and 1.0 mM (Line 7-32) Intrepid® (FIG. 7B). For example, the average PHB content of Line 12-119 plants increased from 0.43±0.17% dwt PHB in untreated plants to 2.12±0.60 and 4.02±0.82% dwt PHB in plants drenched with 0.1 mM and 0.50 mM Intrepid®, respectively. In all cases, polymer production in plants root drenched with Intrepid® exceeded that observed with Mimic® treated plants (FIG. 7A-B). This finding, in conjunction with the higher predicted water solubility of methoxyfenozide, indicates that foliar applications of Intrepid® is capable of inducing higher levels of PHB than those observed with root drenching techniques of Intrepid® and Mimic®.

Figure 7C:
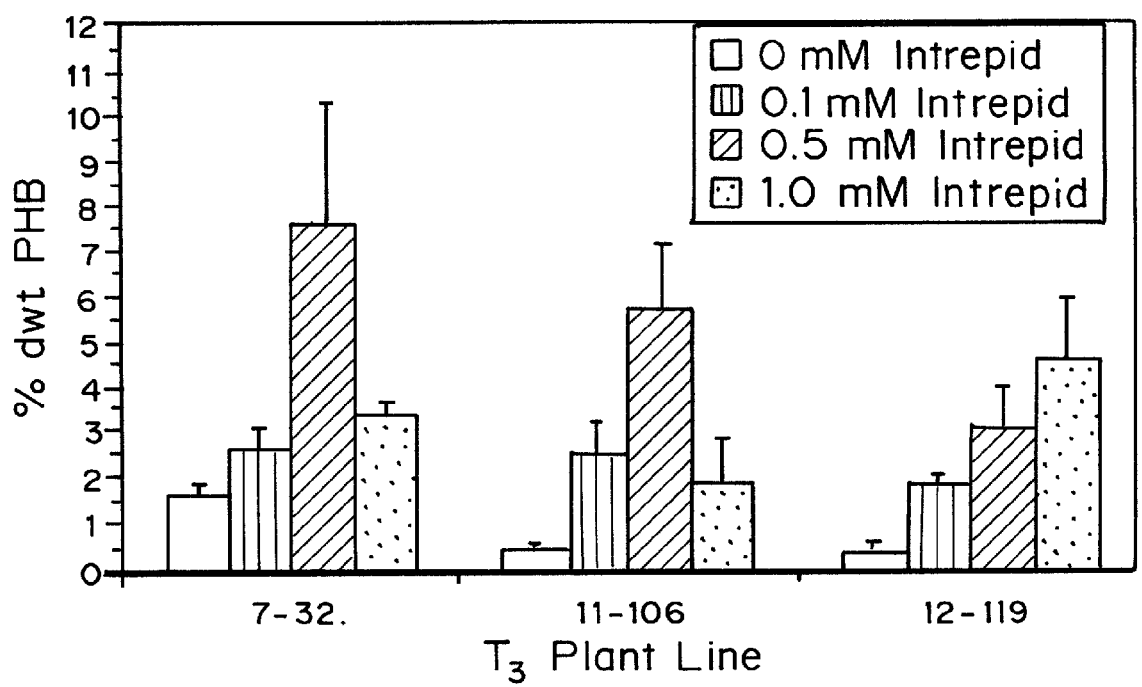

$T_3$ 3I plant Lines 7-32, 11-106 and 12-119 were treated with foliar applications of 0 to 1.0 mM Intrepid®. The application of 0.5 mM Intrepid® was sufficient to induce the highest polymer yields in plant Lines 7-32 and 11-106, but 1.0 mM Intrepid® was required to induce the best PHB yield in plant Line 12-119 (FIG. 7C). For example, the average PHB content of Line 7-32 plants increased from 1.65±0.23% dwt PHB in untreated plants to 2.59±0.41 and 7.57±2.60% dwt PHB in plants sprayed with 0.1 mM and 0.5 mM Intrepid® respectively. The best $T_3$ plant, designated 3I-7-32-5, accumulated 11.5% dwt. PHB overall when sprayed with 0.5 mM Intrepid®. Overall, plants treated with foliar applications of Intrepid® accumulated more PHB than plants root drenched with either Mimic® or Intrepid® (FIG. 7A-C). The 3I-7-32-5 plant did not exhibit the distinctive stunted chlorotic young leaf phenotype of its parent, but appeared to accumulate PHB in relatively normal sized chlorotic young and medium aged leaves. Older leaves remained predominantly green, but did exhibit some chlorosis characteristic of PHB production.

Collectively, these results reveal that careful selection of plants through multiple generations, combined with optimization of inducing agent concentration, composition, and delivery method, can result in an increase in total polymer yield. In addition, these results confirm that the entire pathway involved in PHB production can be induced by foliar applications of a commercial pesticide.

Those skilled in the art will recognize, or be able to ascertain using no more than routine experimentation, many equivalents to the specific embodiments of the invention described herein. Such equivalents are intended to be encompassed by the following claims.

---

We claim:

1. A recombinant vector for the expression of a polyhydroxyalkanoate biosynthetic pathway comprising three or more elements in a plant,
wherein each element comprises operatively linked in the 5' to 3' direction:
a chemically inducible promoter that directs transcription of a nucleic acid sequence;
a nucleic acid sequence encoding a protein; and
a 3' polyadenylation signal sequence,
wherein the nucleic acid sequences encode proteins selected from the group consisting of beta-ketothiolase, acetoacetyl-CoA reductase, PHB synthase, PHA synthase, threonine dehydratase, 3 hydroxy acyl ACP dehydratase, Δ 3-cis, Δ 2-trans isomerase, propionyl-CoA synthetase, hydroxyacyl-CoA synthetase, hydroxyacyl-CoA transferase, thioesterase, fatty acid synthesis enzymes and fatty acid beta-oxidation enzymes.

2. The recombinant vector of claim 1, wherein the inducible promoter in each element is selected from the group consisting of a tetracycline-inducible, pristamycin-inducible, pathogen-inducible, glucocorticoid-inducible, estrogen-inducible, copper-inducible, herbicide safener-inducible, ethanol-inducible, iso-propyl β-D-1-thiogalactopyranoside-inducible, and ecdysone-inducible promoter.

3. The recombinant vector of claim 2, wherein the promoter is an ecdysone-inducible promoter activated by a compound selected from the group consisting of ecdysone, tebufenozide, methoxyfenozide, muristerone A, ponasterone A, insect steroid hormone 20-hydroxyecdysone, and caged β-ecdysone.

4. The recombinant vector of claim 1, wherein the promoter in each element is the same promoter.

5. The recombinant vector of claim 1, wherein the promoter in each element is a different promoter.

6. The recombinant vector of claim 1 for the expression of enzymes in a polyhydroxyalkanoate biosynthetic pathway comprising three or more elements,
wherein each element comprises operatively linked in the 5' to 3' direction;
a promoter activated by an activator molecule or complex that directs transcription of a nucleic acid sequence;
a nucleic acid sequence encoding a protein; and
a 3' polyadenylation signal sequence,
wherein the three or more elements contain nucleic acid sequences encoding beta-ketothiolase, acetoacetyl-CoA reductase, PHB synthase, PHA synthase, threonine dehydratase, 3 hydroxy acyl ACP dehydratase, Δ 3-cis, Δ2-isomerase, propionyl-CoA synthetase, hydroxyacyl-CoA synthetase, hydroxyacyl-CoA transferase, thioesterase, fatty acid synthesis enzymes and fatty acid beta-oxidation enzymes.

7. The recombinant vector of claim 6, wherein the promoter is a tetracycline-responsive promoter.

8. The vector of claim 6, for expression in plants.

9. A transformed plant or plant cell comprising a recombinant vector for expression of proteins in the transformed plant or plant cell, the vector encoding a polyhydroxyalkanoate biosynthetic pathway comprising three or more elements,
wherein each element comprises operatively linked in the 5' to 3' direction:
a chemically inducible promoter that directs transcription of a nucleic acid sequence;
a nucleic acid sequence encoding a protein; and
a 3' polyadenylation signal sequence, wherein the nucleic acid sequences encoding proteins selected from the group consisting of beta-ketothiolase, acetoacetyl-CoA reductase, PHB synthase, PHA synthase, threonine dehydratase, 3 hydroxy acyl ACP dehydratase, Δ 3-cis, Δ 2-isomerase, propionyl-CoA synthetase, hydroxyacyl-CoA synthetase, hydroxyacyl-CoA transferase, thioesterase, fatty acid synthesis enzymes and fatty acid beta-oxidation enzymes, and wherein the transformed plant produces at least 10% dry weight (dwt) polyhydroxyalkanoate after inducing the inducible promoters, and wherein the plant does not exhibit a stunted chiorotic phenotype.

10. The transformed plant cell of claim 9, wherein the inducible promoter in each element is selected from the group consisting of a tetracycline-inducible, pristamycin-inducible, pathogen-inducible, glucocorticoid-inducible, estrogen-inducible, copper-inducible, herbicide safener-inducible, ethanol-inducible, iso-propyl β-D-1-thiogalactopyranoside-inducible, and ecdysone-inducible promoter.

11. The transformed plant cell of claim 10, wherein the promoter is an ecdysone-inducible promoter activated by a compound selected from the group consisting of ecdysone, tebufenozide, methoxyfenozide, muristerone A, ponasterone A, insect steroid hormone 20-hydroxyecdysone, and caged β-ecdysone.

12. The transformed plant cell of claim 9, wherein the promoter in each element is the same promoter.

13. The transformed plant cell of claim 9, wherein the promoter is an ecdysone-inducible promoter.

14. The transformed plant cell of claim 9, wherein the promoter in each element is different.

15. A transformed plant or plant cell comprising a recombinant vector for expression of proteins in the transformed plant or plant cell, the vector encoding a polyhydroxyalkanoate biosynthetic pathway comprising three or more elements,
wherein each element comprises operatively linked in the 5' to 3' direction;
a promoter activated by an activator molecule or complex that directs transcription of a nucleic acid sequence;
a nucleic acid sequence encoding a protein; and
a 3' polyadenylation signal sequence,
wherein the nucleic acid sequences encode proteins selected from the group consisting of beta-ketothiolase, acetoacetyl-CoA reductase, PHB synthase, PHA synthase, threonine dehydratase, 3 hydroxy acyl ACP dehydratase, Δ 3-cis, Δ 2-isomerase, propionyl-CoA synthetase, hydroxyacyl-CoA synthetase, hydroxyacyl-CoA transferase, thioesterase, fatty acid synthesis enzymes and fatty acid beta-oxidation enzymes, wherein the transformed plant produces at least 10% dwt polyhydroxyalkanoate after inducing the inducible promoters and, wherein the plant or plant cell does not exhibit a stunted chiorotic phenotype.

16. The transformed plant cell of claim 15, wherein the promoter is a tetracycline-responsive promoter.

17. A method for the production of a polyhydroxyalkanoate in a plant comprising a) introducing into the plant, a recombinant vector comprising three or more elements, wherein each element comprises operatively linked in the 5' to 3' direction:
a chemically inducible promoter that directs transcription of a nucleic acid sequence;
a nucleic acid sequence encoding a protein; and
a 3' polyadenylation signal sequence,
wherein the three or more elements contain nucleic acid sequences that encode proteins selected from the group consisting of beta-ketothiolase, acetoacetyl-CoA reductase, PHB synthase, PHA synthase, threonine dehydratase, 3 hydroxy acyl ACP dehydratase, Δ 3-cis, Δ 2-isomerase, propionyl-CoA synthetase, hydroxyacyl-CoA synthetase, hydroxyacyl-CoA transferase, thioesterase, fatty acid synthesis enzymes and fatty acid beta-oxidation enzymes, and
b) activating the inducible promoters with an inducing agent,
wherein the plant produces at least 10% dwt polyhydroxyalkanoate after activating the inducible promoters and, wherein the plant does not exhibit a stunted chlorotic phenotype.

18. The method of claim 17, wherein the inducible promoter in each element is selected from the group consisting of a tetracycline-inducible, pristamycin-inducible, pathogen-inducible, glucocorticoid-inducible, estrogen-inducible, copper-inducible, herbicide safener-inducible, ethanol-inducible, iso-propyl β-D-1-thiogalactopyranoside-inducible, and ecdysone-inducible promoter.

19. The method of claim 18, wherein the inducible promoter is an ecdysone-inducible promoter activated by a compound selected from the group consisting of ecdysone, tebufenozide, methoxyfenozide, muristerone A, ponasterone A, insect steroid hormone 20-hydroxyecdysone, and caged β-ecdysone.

20. The method of claim 17, wherein the promoter in each element is the same promoter.

21. The method of claim 17, wherein the promoter in each element is a different promoter.

22. The method of claim 17 wherein the inducible promoter is activated by a chemical through a foliar spray or root drenching.

23. The plant of claim 9 selected from the group consisting of *Brassica; Arabidopsis*; maize; soybean; cottonseed; sunflower; palm; coconut; safflower; peanut; mustards, alfalfa, switchgrass, sorghum and tobacco.

24. The method of claim 17 wherein the plant is selected from the group consisting of *Brassica; Arabidopsis*; maize; soybean; cottonseed; sunflower; palm; coconut; safflower; peanut; mustards, alfalfa, switchgrass, sorghum and tobacco.

25. The vector of claim 1 encoding a β-ketothiolase (thiolase), an NADPH-acetoacetyl-CoA reductase (reductase) and a PHA synthase (synthase).

26. The plant of claim 9 encoding a β-ketothiolase (thiolase), an NADPH-acetoacetyl-CoA reductase (reductase) and a PHA synthase (synthase).

* * * * *

UNITED STATES PATENT AND TRADEMARK OFFICE
CERTIFICATE OF CORRECTION

| | | |
|---|---|---|
| PATENT NO. | : 7,732,680 B2 | Page 1 of 1 |
| APPLICATION NO. | : 11/376831 | |
| DATED | : June 8, 2010 | |
| INVENTOR(S) | : Lauralynn Kourtz, Oliver Peoples and Kristi Snell | |

It is certified that error appears in the above-identified patent and that said Letters Patent is hereby corrected as shown below:

Claim 9, line 12, column 29, replace "chiorotic" with --chlorotic--.
Claim 15, line 54, column 29, replace "chiorotic" with --chlorotic--.

Signed and Sealed this
Seventeenth Day of May, 2011

David J. Kappos
*Director of the United States Patent and Trademark Office*